United States Patent
Chaudhary et al.

(10) Patent No.: US 9,849,036 B2
(45) Date of Patent: *Dec. 26, 2017

(54) IMAGING-CONTROLLED LASER SURGICAL SYSTEM

(71) Applicant: ALCON LENSX, INC., Aliso Viejo, CA (US)

(72) Inventors: Gautam Chaudhary, Laguna Hills, CA (US); Peter Goldstein, Santa Ana, CA (US); Imre Hegedus, Aliso Viejo, CA (US); Carlos German Suarez, Tustin, CA (US); David Calligori, Rancho Santa Margarita, CA (US); Michael Karavitis, San Pedro, CA (US)

(73) Assignee: ALCON LENSX, INC., Aliso Viejo, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/452,252

(22) Filed: Mar. 7, 2017

(65) Prior Publication Data
US 2017/0172803 A1 Jun. 22, 2017

Related U.S. Application Data

(63) Continuation of application No. 13/110,352, filed on May 18, 2011, now Pat. No. 9,622,913.

(51) Int. Cl.
*A61F 9/008* (2006.01)
*A61B 18/00* (2006.01)

(52) U.S. Cl.
CPC ............ *A61F 9/00825* (2013.01); *A61B 2018/00636* (2013.01); *A61F 2009/0087* (2013.01); *A61F 2009/00844* (2013.01); *A61F 2009/00851* (2013.01); *A61F 2009/00889* (2013.01)

(58) Field of Classification Search
CPC .......... A61F 2009/0087; A61F 9/008; A61F 2009/00851; A61F 2009/00889; A61F 9/00825; A61B 2018/00636; A61F 2009/00844
See application file for complete search history.

(56) References Cited

U.S. PATENT DOCUMENTS

| | | | |
|---|---|---|---|
| 2010/0042079 A1* | 2/2010 | Frey | A61F 9/008 606/4 |
| 2011/0202046 A1* | 8/2011 | Angeley | G06T 7/149 606/6 |

* cited by examiner

*Primary Examiner* — Scott T Luan
(74) *Attorney, Agent, or Firm* — S. Brannon Latimer

(57) ABSTRACT

An imaging-based laser system can include a laser-beam system, configured to generate and scan a beam of laser pulses with an adjustable laser-power parameter to points of a scan-pattern in an eye, and an imaging-based laser-controller, configured to image a layer in the eye, to control the scanning of the beam of laser pulses to the points of the scan-pattern, and to control a laser-power parameter of the laser pulses according to the distance of the points of the scan-pattern from the imaged layer.

17 Claims, 26 Drawing Sheets

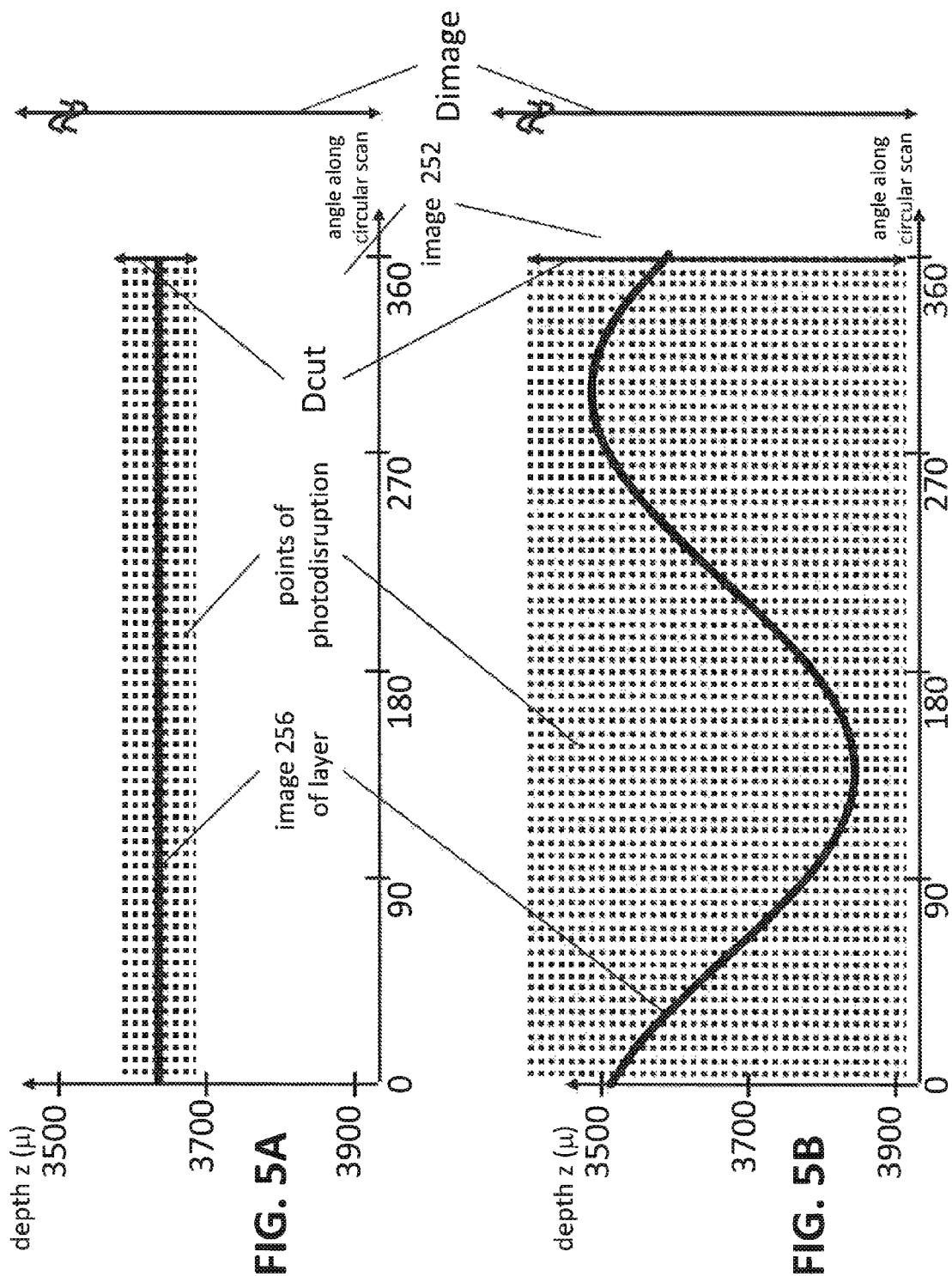

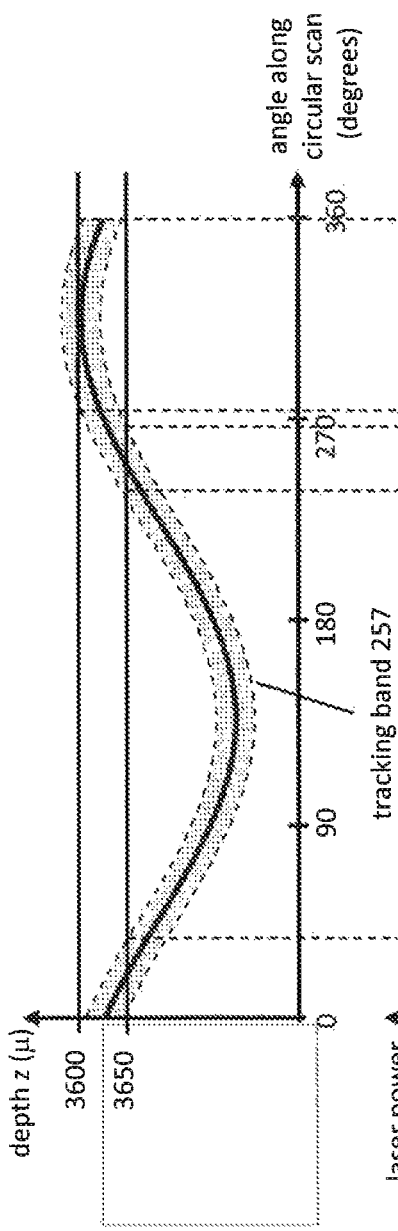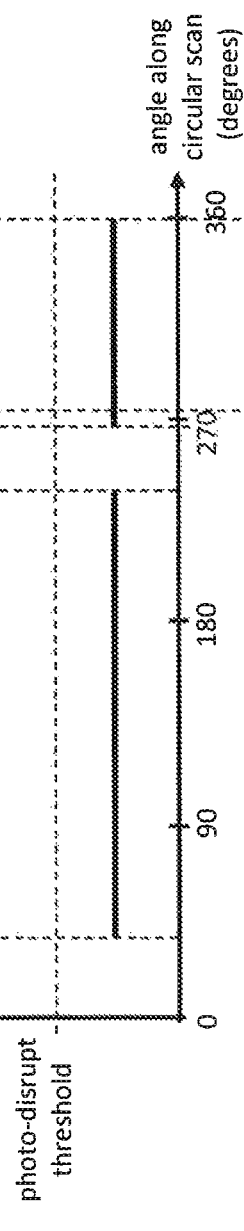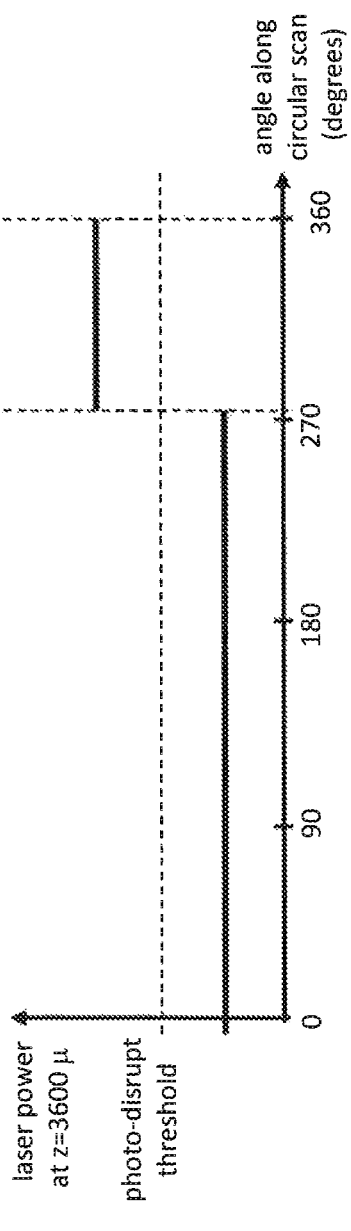

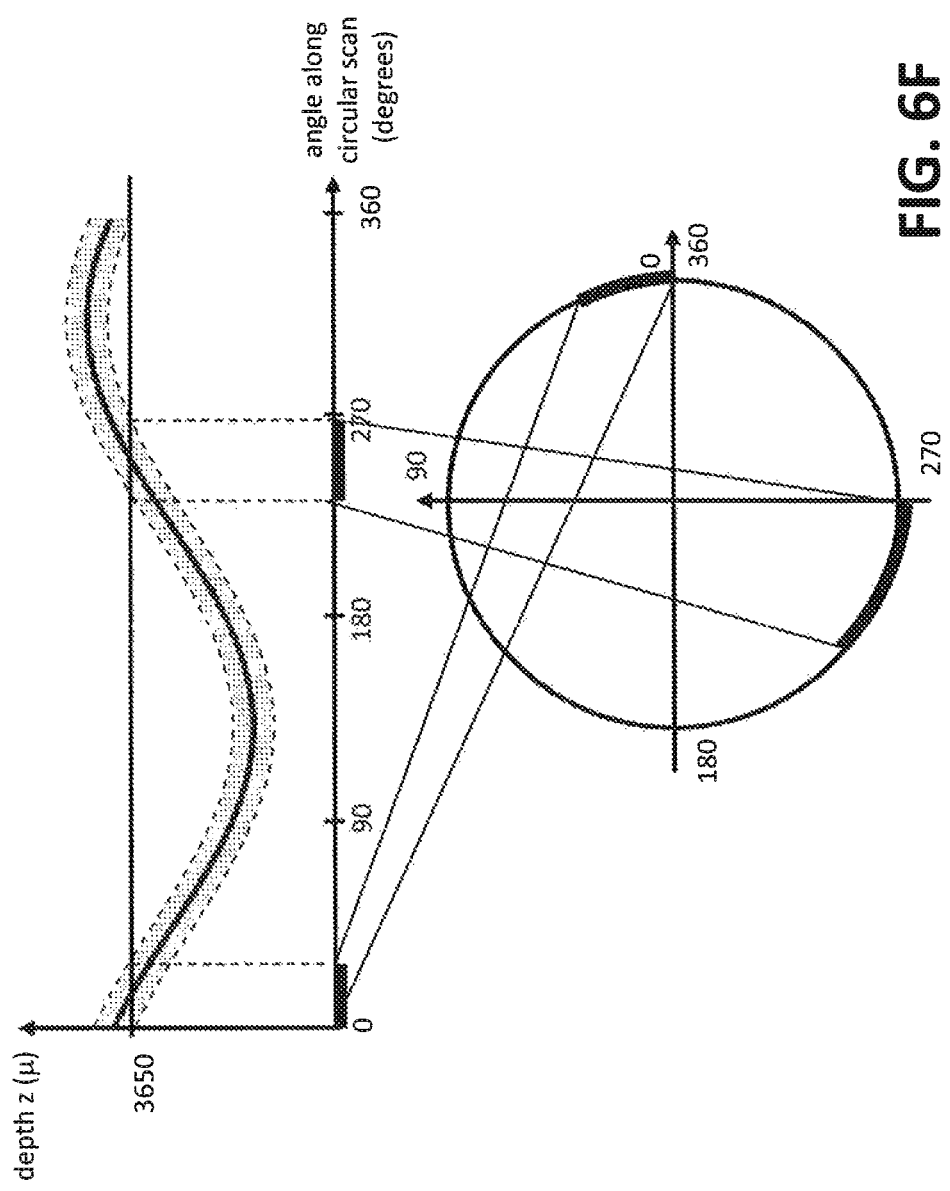

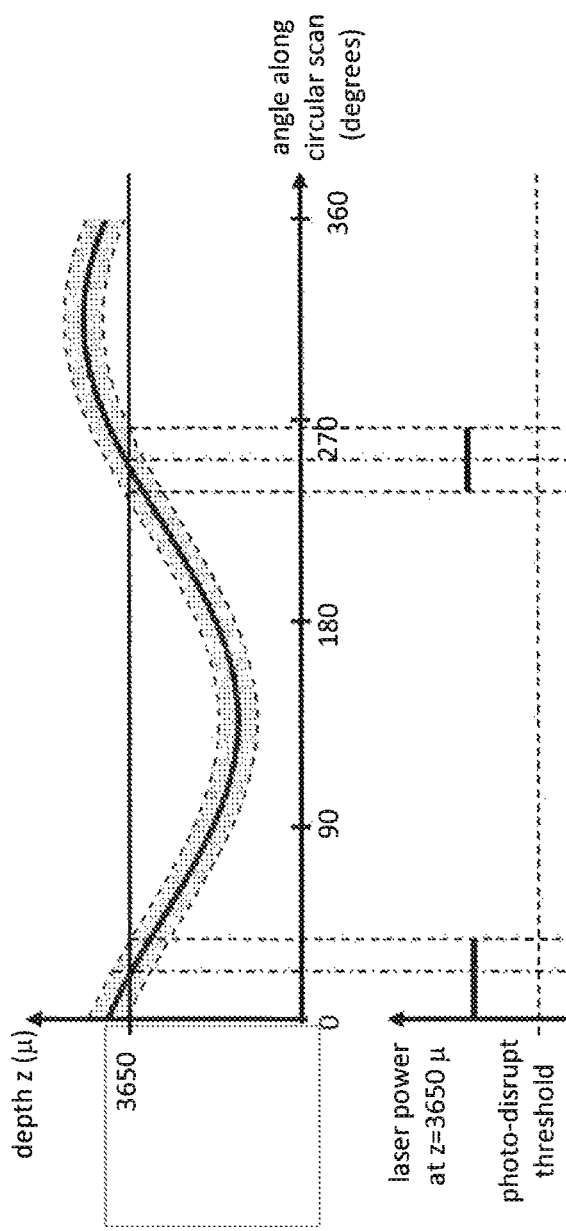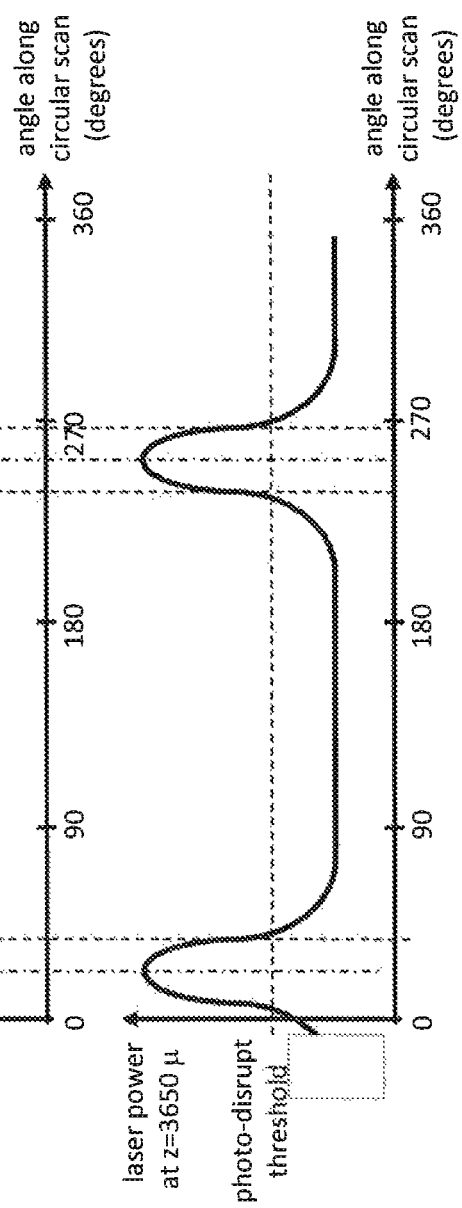
FIG. 6G
FIG. 6H

IMAGING-CONTROLLED LASER SURGICAL SYSTEM

TECHNICAL FIELD

This patent document describes a system and method for controlling a laser in an ophthalmic procedure. In more detail, this patent document describes an imaging-controlled laser system for controlling the power of a pulsed ophthalmic laser during capsulotomy and cataract procedures, among others.

BACKGROUND

Laser systems have become essential for ophthalmic surgery. They have been employed in corneal procedures for some time now with high precision and therefore considerable success. In very recent times applications for other ophthalmic procedures have been contemplated, including cataract procedures.

Lasers can be used for forming high precision cuts. These cuts are created by focusing or directing a rapid sequence of laser pulses to a scan-pattern or point-pattern. The points of the scan-pattern often form a line or layer and the laser pulses are directed to these points by a scanning system that includes deflection devices, mirrors and lenses whose alignment can be changed very quickly. In typical laser systems the pulses can have a duration or pulse length in the nanosecond, picosecond, or even femtosecond range. The pulse repetition rate can be in the kHz to hundreds of kHz range.

The power or energy of the laser pulses can be chosen to exceed a so-called photodisruption threshold. Laser pulses with a power above this threshold can disrupt the ophthalmic tissue at the target points, inducing the formation of bubbles. Lines or layers of these bubbles can weaken the mechanical connection between the tissue-portions on the opposite sides of the bubbles. Often the weakening is substantial, effectively cutting the tissue. Therefore, a subsequent manual procedure can completely separate the tissue portions with ease.

One ophthalmic procedure which could benefit from using such a high precision laser cutting system is cataract surgery. A typical cataract surgery involves a capsulotomy step and a lysis or lens fragmentation step. During lysis, energy is applied to a lens nucleus to liquefy it. During lens fragmentation, or phaco-fragmentation, the nucleus of the lens can be cut into several pieces by scanning the laser along cutting surfaces to enable the subsequent piece-by-piece removal of the nucleus. The capsulotomy involves forming a circular cut on the anterior portion of the capsular bag of the lens to allow the surgeon to access and remove the cut-up pieces of the nucleus.

To optimize surgical laser systems for these complex ophthalmic procedures is a great challenge. However, the optimization promises great returns in terms of the precision and efficacy of the surgical procedures.

SUMMARY

One of the challenges of laser cataract surgery is that the procedures of capsulotomy and lens fragmentation can interfere with each other. In advanced laser systems the precision of the surgery can be enhanced by imaging the ophthalmic target tissue prior to the surgery and guide the laser pulses based on the image. If the lens fragmentation is performed first, then, as a surgical by-product, the capsule is expanded considerably and unevenly by the substantial amount of bubbles formed inside the capsule. Therefore, after the lens fragmentation, the capsule and lens has to be imaged for a second time to guide the subsequent circular cut of the capsulotomy. However, imaging the severely photodisrupted and distorted lens can be challenging. Also, the repeated imaging procedure consumes precious surgical time, increasing the discomfort of the patient, potentially undermining the precision of the entire procedure.

On the other hand, if the capsulotomy is performed first, it creates a substantial amount of bubbles in the anterior region of the lens and in the anterior aqueous chamber of the eye. The amount of bubbles is especially high if the lens is in a tilted position before the procedure, as explained below. These bubbles can increase the scattering of the laser pulses of the subsequent lens fragmentation considerably as the subsequent pulses are directed to the inside of the lens and thus propagate through the bubble-rich anterior region. The increased scattering can again potentially undermine the precision of the cataract procedure.

Thus, both sequences of the lens fragmentation and capsulotomy have drawbacks, as the first step can reduce the precision and control of the subsequent step. Therefore, laser systems that reduce, resolve, or eliminate one or more of these drawbacks can offer advantages.

Embodiments of the present invention can provide advantageous functionalities in view of these challenges. In particular, an embodiment of an imaging-based laser system can include a laser-beam system, configured to generate and scan a beam of laser pulses with an adjustable laser-power parameter to points of a scan-pattern in an eye, and an imaging-based laser-controller, configured to image a layer in the eye, to control the scanning of the beam of laser pulses to the points of the scan-pattern, and to control a laser-power parameter of the laser pulses according to the distance of the points of the scan-pattern from the imaged layer.

An implementation of an imaging-based laser system can include a laser that generates and directs a beam of laser pulses into an eye, an imaging system that images a capsule layer of the eye, and a laser control system that controls the laser to direct the beam to spots within a tracking band of the imaged capsule layer with a laser-power parameter above a photo-disruption threshold, and to spots outside the tracking band of the imaged capsule layer with a laser-power parameter below a photo-disruption threshold, wherein the image-based laser system is configured to perform a capsulotomy before a lysis or lens- or phaco-fragmentation during a cataract procedure.

An implementation of an image-guided ophthalmic laser system can include a laser engine, configured to generate laser pulses, a beam modifier, configured to modify a laser-power parameter of the laser pulses, a laser scanner, configured to direct the laser pulses to scanning-points in an eye, an imaging system, configured to image a region in the eye, and a pattern generator, coupled to the imaging system, the beam modifier and the laser scanner, configured to generate coordinates of the scanning-points for the laser scanner, and to associate a laser-power parameter with the scanning-points depending on a distance of the scanning-points from a target-pattern.

In some implementations, a method of performing an imaging-controlled ophthalmic procedure can include imaging a layer in an eye, generating coordinates of points of a scan-pattern, determining a distance of the points of the scan-pattern from the imaged layer, and associating laser-power parameters with the points based on the determined distance.

BRIEF DESCRIPTION OF THE DRAWINGS

FIGS. 5A-B illustrate traditional scan-patterns for non-tilted and tilted lenses as a function of a scanning variable.

FIGS. 6A-H illustrate a scan-pattern along a circular scan with a distance-dependent laser-power parameter.

DETAILED DESCRIPTION

Implementations and embodiments described in this patent document offer improvements for the above described challenges.

Figure 1:
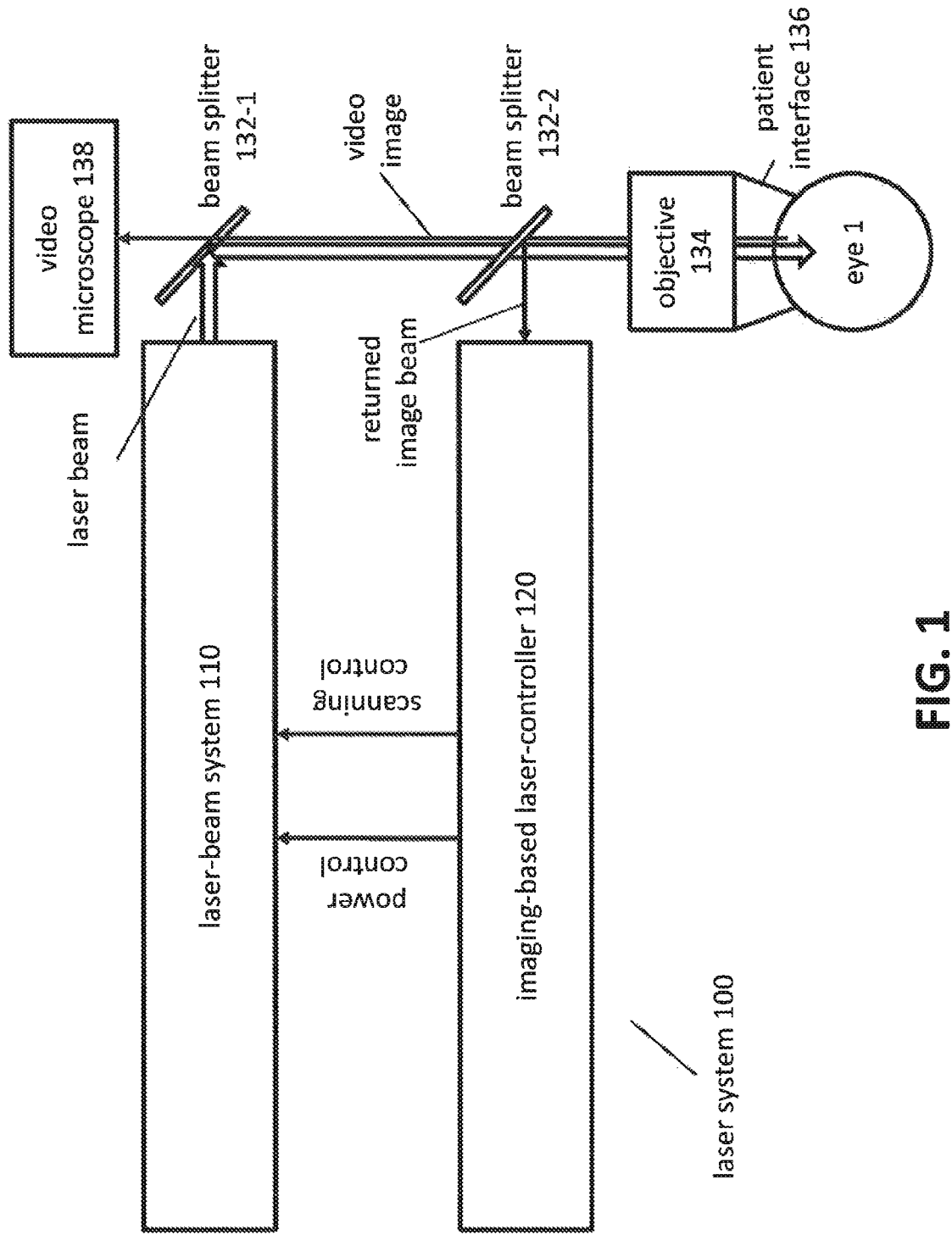
FIG. 1 illustrates an embodiment of a surgical laser system with an imaging-controlled laser system

FIG. 1 illustrates an imaging-based laser system 100, including a laser-beam system 110 to generate and scan a beam of laser pulses with an adjustable laser-power parameter to points of a scan-pattern in an eye 1, and an imaging-based laser-controller 120 to image a layer in the eye, to control the scanning of the beam of laser pulses to the points of the scan-pattern, and to control a laser-power parameter of the laser pulses according to the distance of the points of the scan-pattern from the imaged layer. The laser-controller 120 can perform these functions by sending a power control signal and a scanning control signal to the laser-beam system 110, for example.

The laser beam of the laser-beam system 110 can be guided into the main optical pathway at a beam-splitter 132-1 that can redirect the beam to an objective 134. The beam can propagate through the objective 134 and through a patient interface 136 to enter into the surgical eye 1.

The surgery can be assisted by imaging the eye 1 with various techniques. A visible imaging light can be used to create a video image that is processed by a video microscope 138. In addition, the imaging-based laser-controller 120 can shine an imaging beam on the eye and form an image based on the returned image beam. This imaging beam can be coupled into and out of the main optical path by a beam-splitter 132-2.

FIGS. 2A-D illustrate various embodiments of the laser-beam system 110.

Figure 2A:
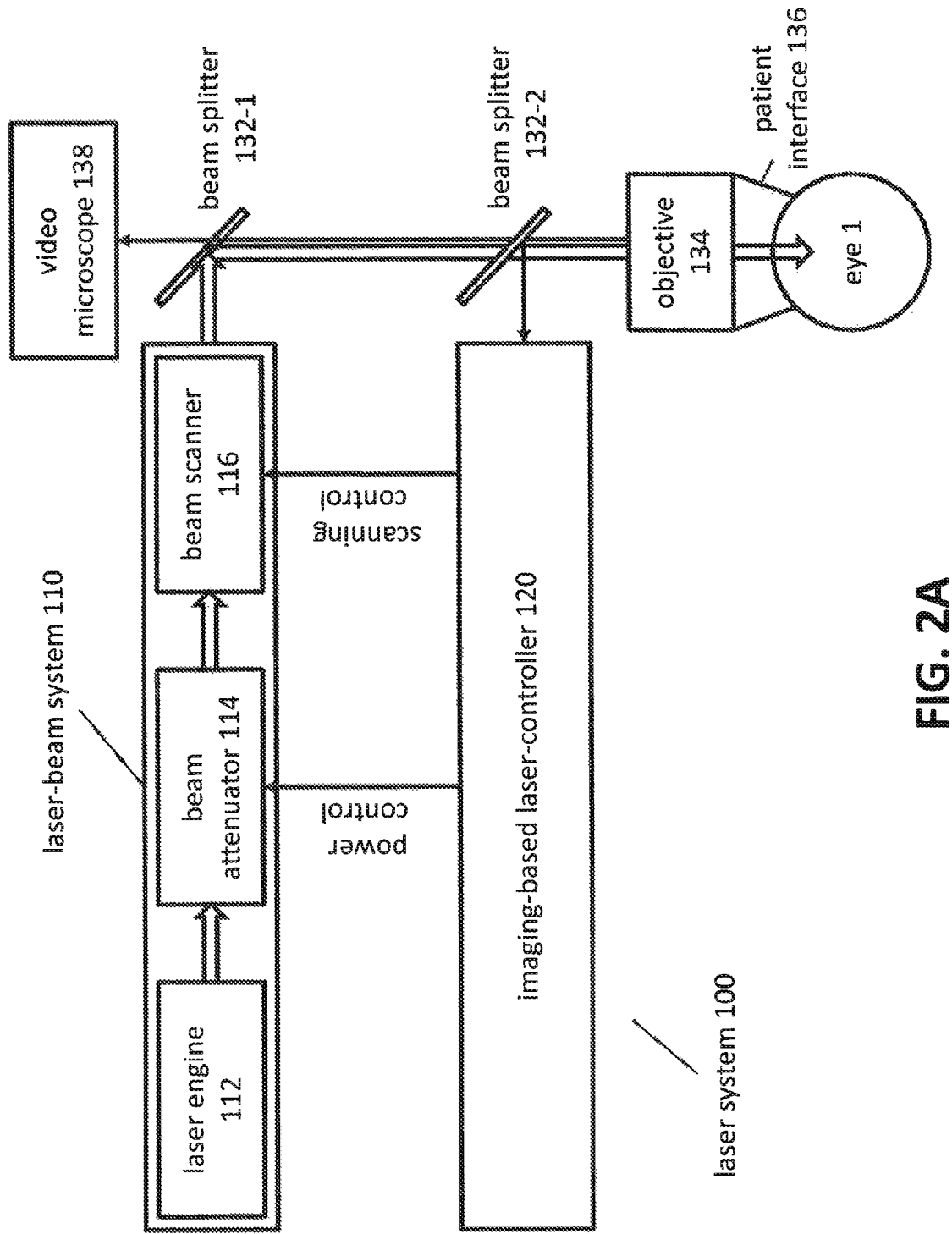
FIGS. 2A-D illustrate embodiments of the laser-beam system.

FIG. 2A illustrates that embodiments of the laser-beam system 110 can include a laser engine 112 to generate the beam of laser pulses, a beam attenuator 114 to modify the laser-power parameter of the laser pulses, and a beam scanner 116 to direct the beam of laser pulses to the points of the scan-pattern in the eye. The laser engine 112 can generate laser pulses with a duration of nanoseconds, picoseconds or even femtoseconds, i.e. in the $10^{-9}$-$10^{-15}$ sec range. These pulses can be generated at a repetition rate in a wide range of frequencies: from 0.1 kHz to 1,000 kHz, or in a range of 1 kHz to 500 kHz, or in some implementations in the 10 kHz to 100 kHz range. The power control signal of the laser-controller 120 can be coupled into the beam attenuator 114 and the scanning control signal of the laser-controller 120 can be coupled into the beam scanner 116.

The beam attenuator 114 can include a Pockels cell, a polarizer-assembly, a mechanical shutter, an electro-mechanical shutter, or an energy wheel. Each of these implementations can modify a laser-power parameter of the laser pulses. The laser-power parameter can be a pulse energy, a pulse power, a pulse length or a pulse repetition rate of the laser pulses, among others. The beam attenuator 114 can modify one or more of these laser-power parameters. In a simple implementation, the beam attenuator 114 can shutter or block selected laser pulses. In another, a polarizer assembly can reduce the power of selected laser pulses by adjusting the relative angle of subsequent polarizing filters.

In the embodiment of FIG. 2A, the beam attenuator 114 can be located between the laser engine 112 and the beam scanner 116 in the path of the laser beam.

Figure 2B:
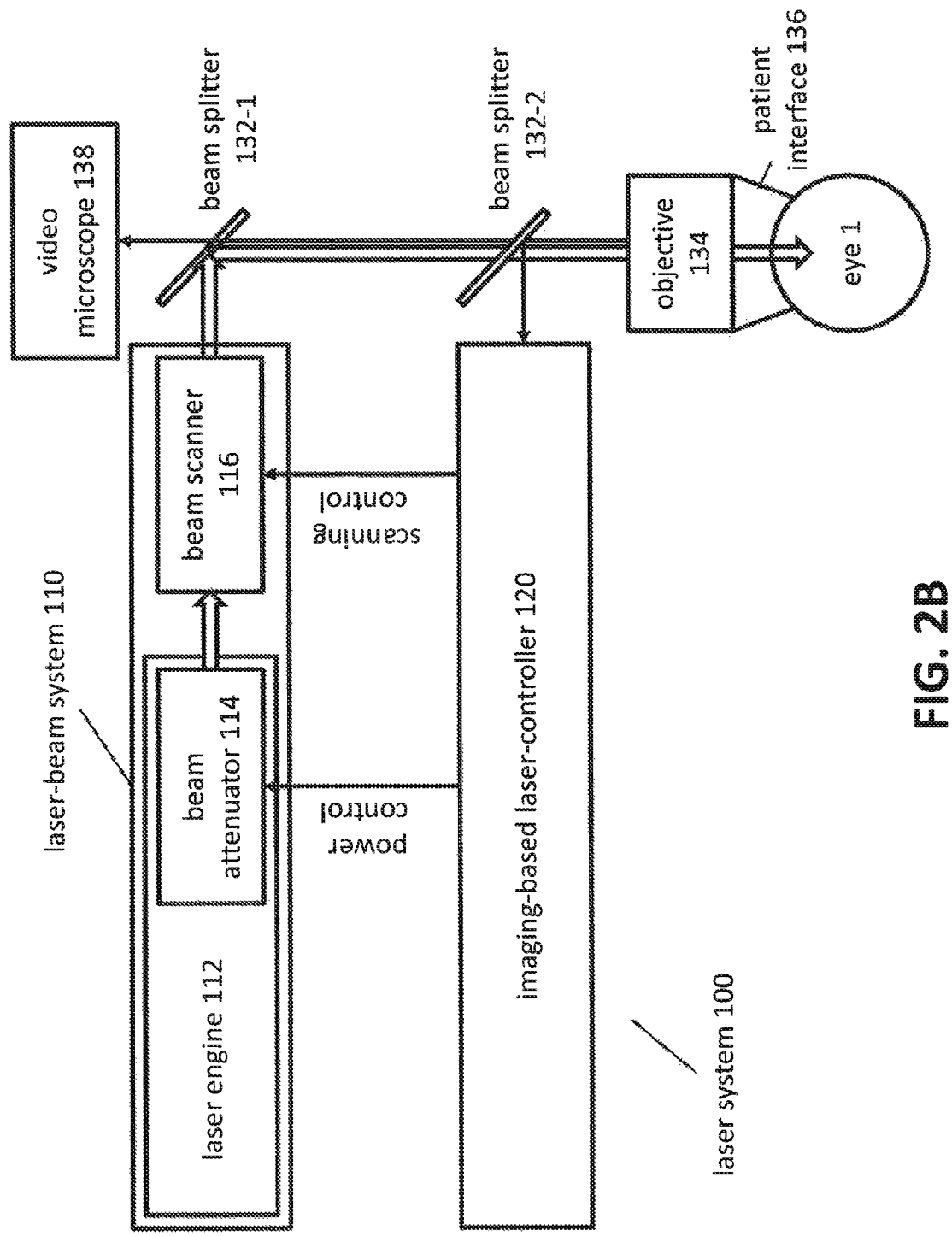

FIG. 2B illustrates and embodiment in which the beam attenuator 114 is at least partially integrated into the laser engine 112. In some cases, the beam attenuator 114 can be part of the laser engine 112. For example, a Pockels cell within the laser engine 112 can be the beam attenuator 114.

Figure 2C:
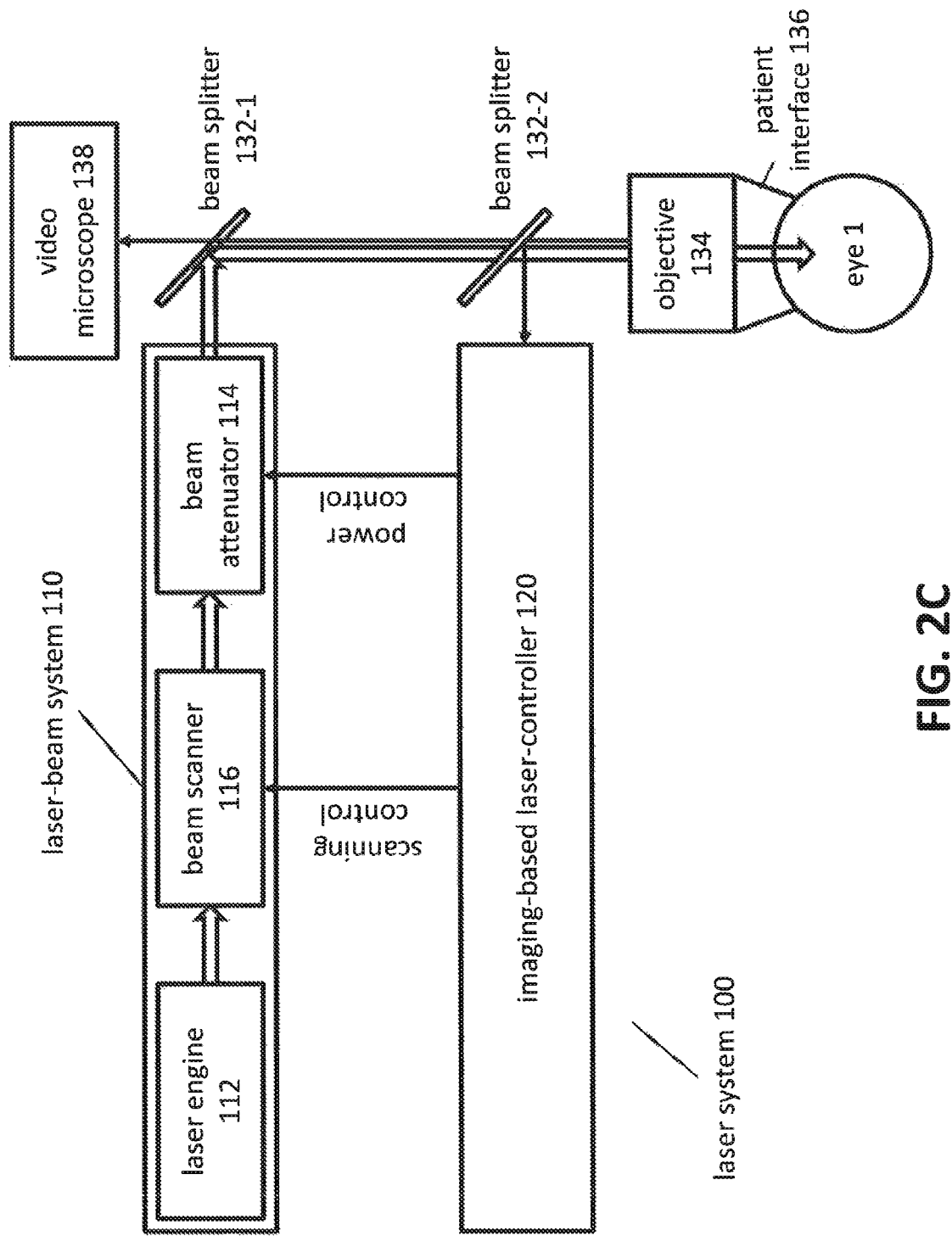

FIG. 2C illustrates and embodiment in which the beam attenuator 114 is located after the beam scanner 116 in the path of the laser beam.

Figure 2D:
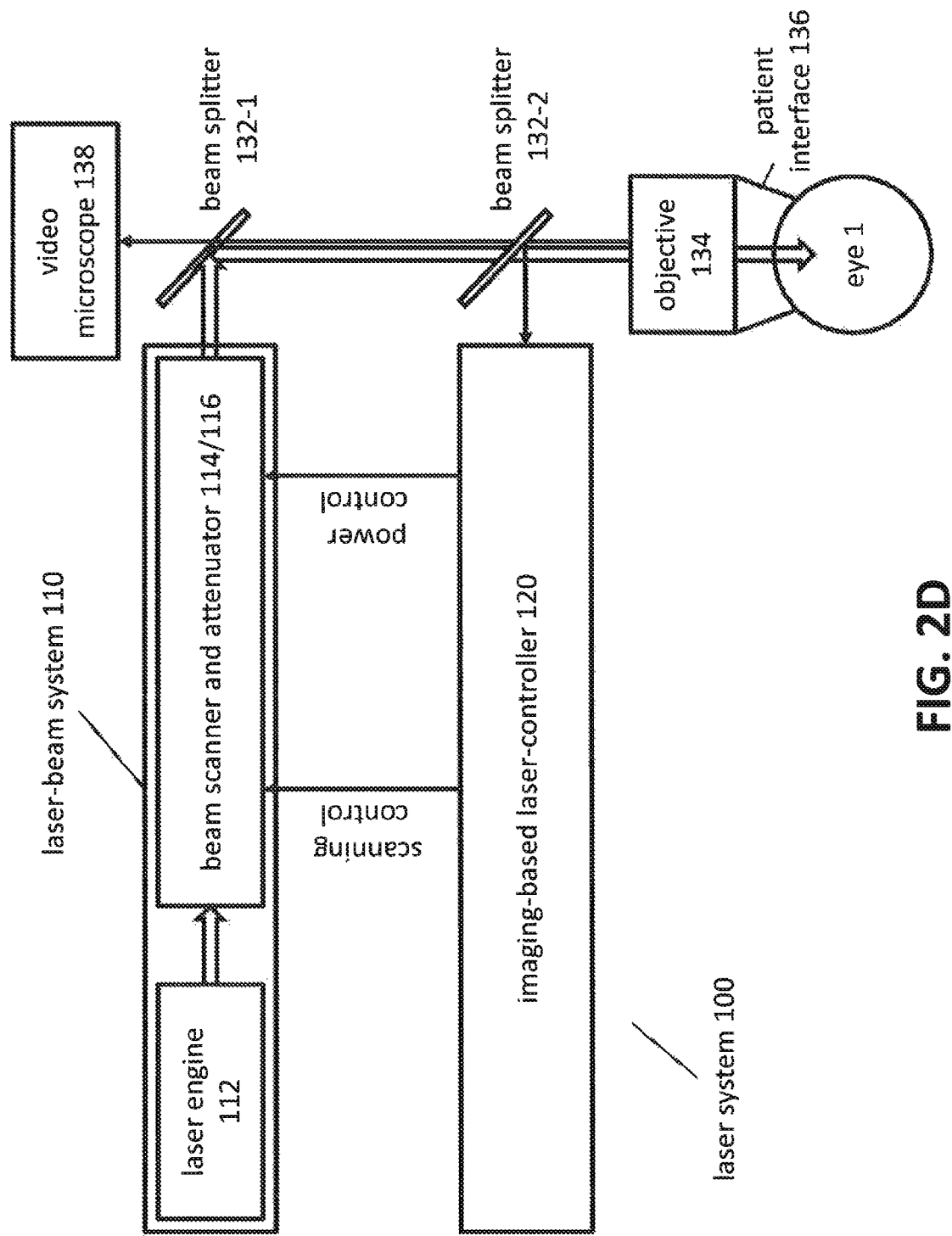

Finally, FIG. 2D illustrates an embodiment in which the beam attenuator 114 and the beam scanner 116 are at least partially integrated.

FIGS. 3A-E illustrate various embodiments of the imaging-based laser-controller 120.

Figure 3A:
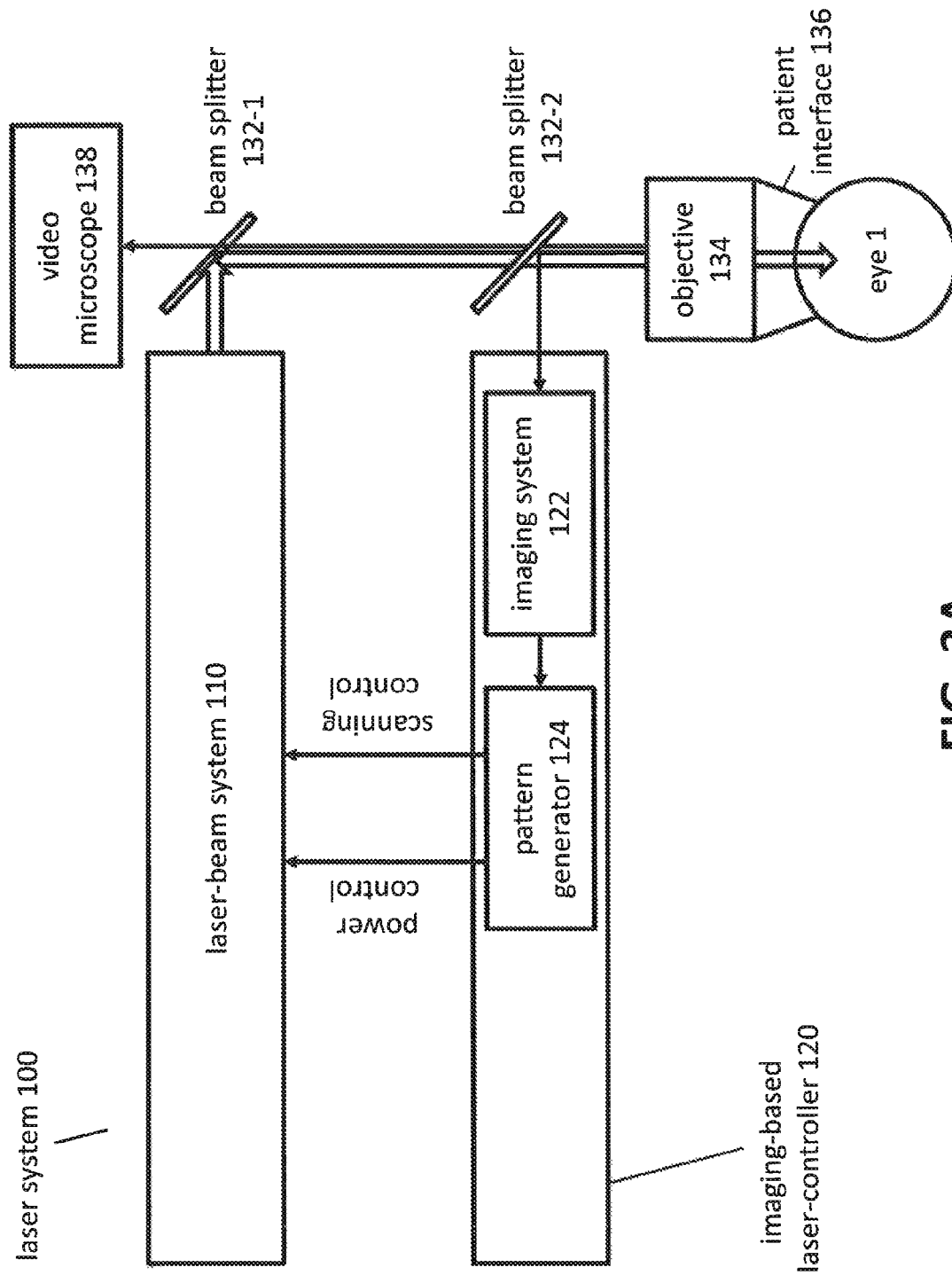
FIGS. 3A-E illustrate embodiments of the imaging-based laser controller.

FIG. 3A illustrates that the laser-controller 120 can include an imaging system 122 to image the imaged layer in the eye and a pattern generator 124 to generate coordinates of the points of the scan-pattern, to associate laser-power parameters with the points depending on the distance of the points from the imaged layer, and to signal the generated coordinates of the points and the corresponding laser-power parameters to the laser-beam system 110. In some implementations, the imaging system 122 can image any ophthalmic target in the anterior or posterior segment of the eye, targets from the cornea to the retina.

The pattern generator 124 can signal the generated coordinates of the points of the scan-pattern to the beam scanner 116 with a scanning control signal. Further, the pattern generator 124 can signal the laser-power parameters corresponding to the points of the scan-pattern to the beam attenuator 114 with a power control signal. The laser-power parameter can be a pulse energy, a pulse power, a pulse length or a pulse repetition rate of the laser pulses.

The imaging system 122 can include an ophthalmic coherence tomography (OCT) system, a Scheimpflug imaging system, a scanning imaging system, a single shot imaging system, an ultrasound imaging system, and a video imaging system. Here, the scanning imaging systems can create the image by scanning an imaging beam, whereas single shot imaging systems can acquire imaging information about an imaged area or volume in a single shot. The OCT system can be a time-domain OCT, a frequency-domain OCT, or a spectrometer-based OCT system, among others.

Figure 3B:
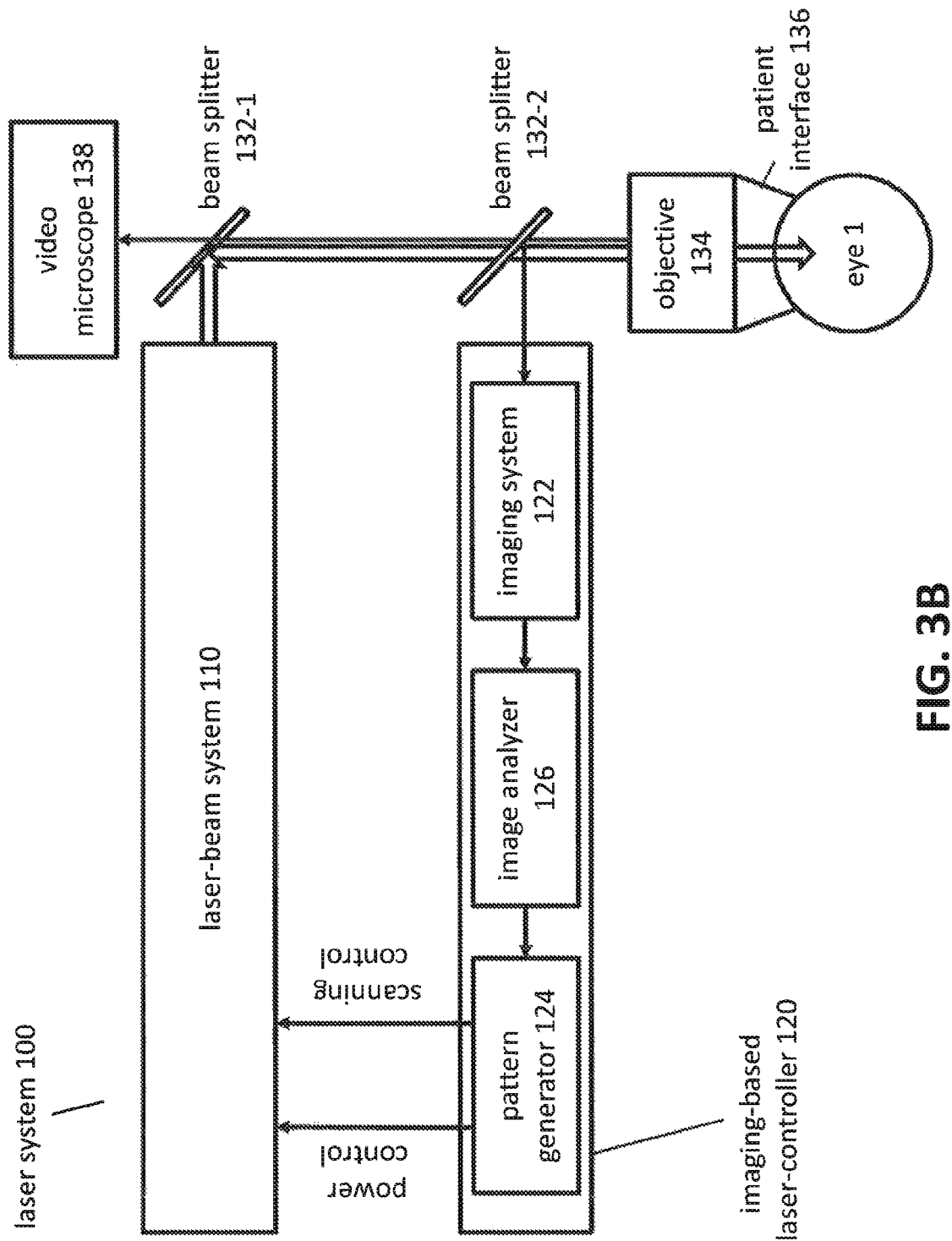

FIG. 3B illustrates that in some implementations the laser-controller 120 can include an image-analyzer 126. The image analyzer 126 can receive the image of the imaged layer from the imaging system 122, perform an analysis of the imaged layer as described below and forward the result of the analysis to the pattern generator 124.

Figure 3C:
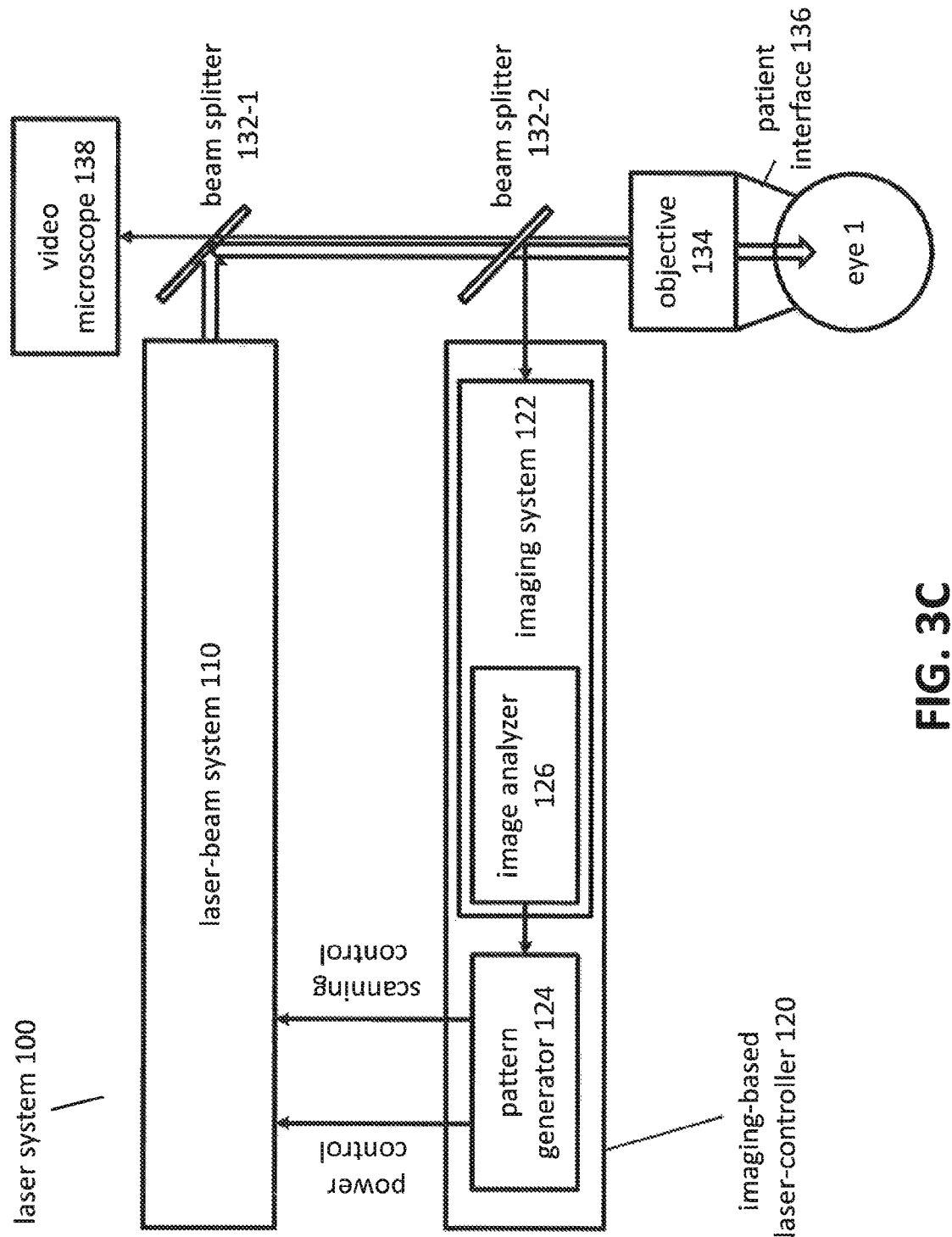
Figure 3D:
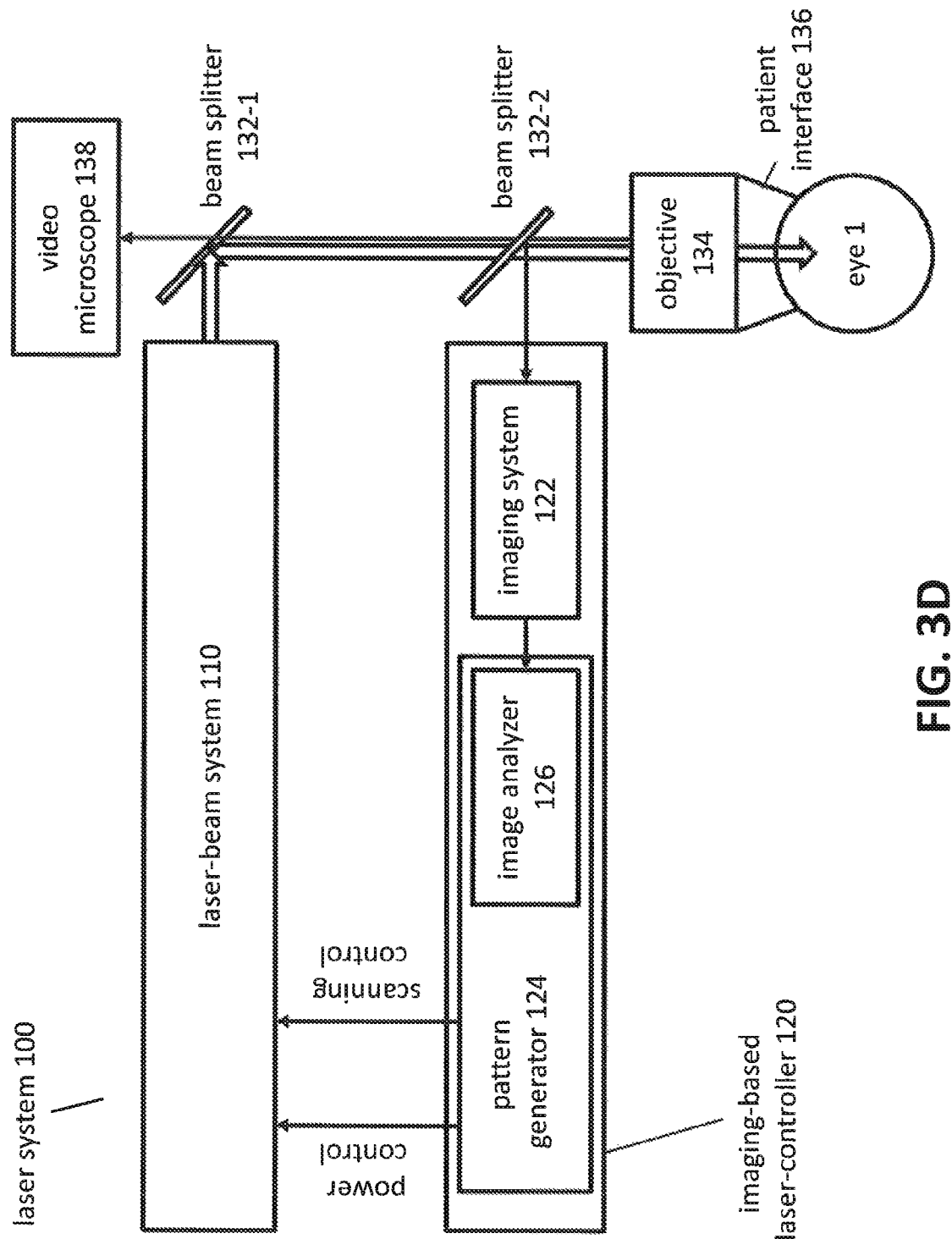

FIG. 3C illustrates that in some implementations the image analyzer 126 can be at least partially integrated with the imaging system 122. FIG. 3D illustrates that in some implementations the image analyzer 126 can be at least partially integrated with the pattern generator 124.

Figure 3E:
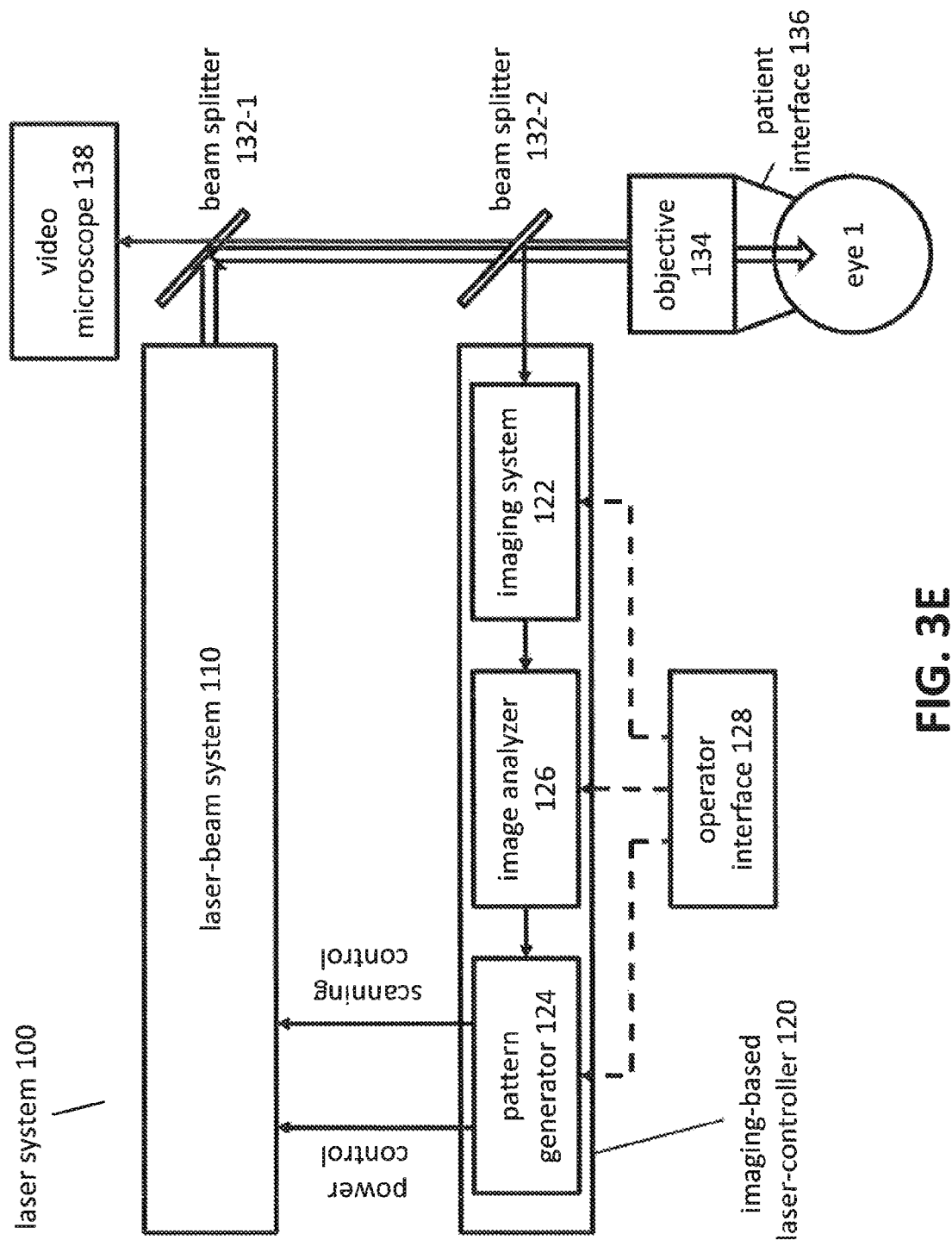

FIG. 3E illustrates that in some embodiments, the laser system 100 can include an operator-interface 128 that can be coupled to one or more of the imaging system 122, the pattern generator 124 and the image analyzer 126.

Figure 4A:
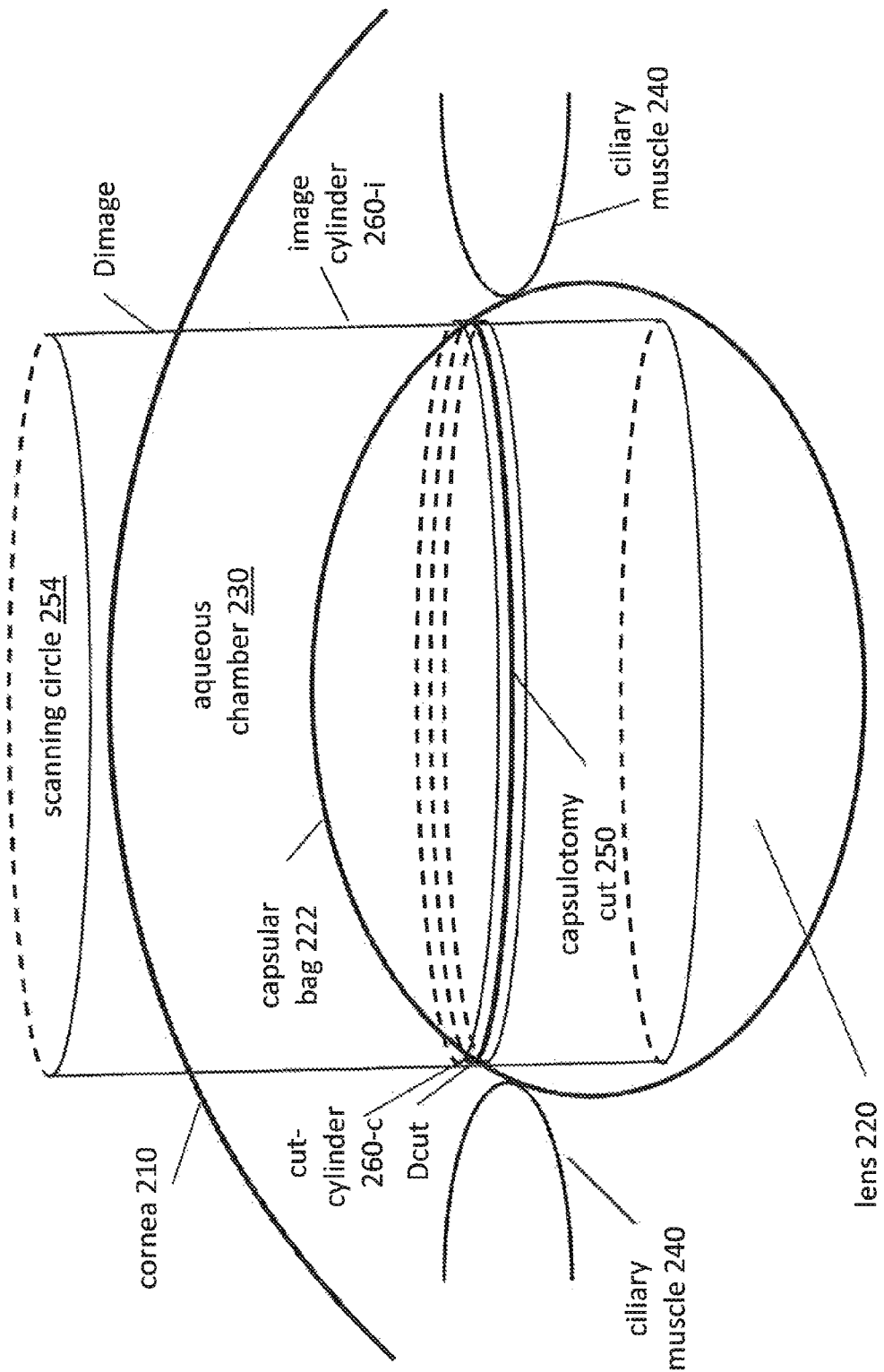
FIGS. 4A-B illustrate the scan-patterns for non-tilted and tilted lenses.
Figure 4B:
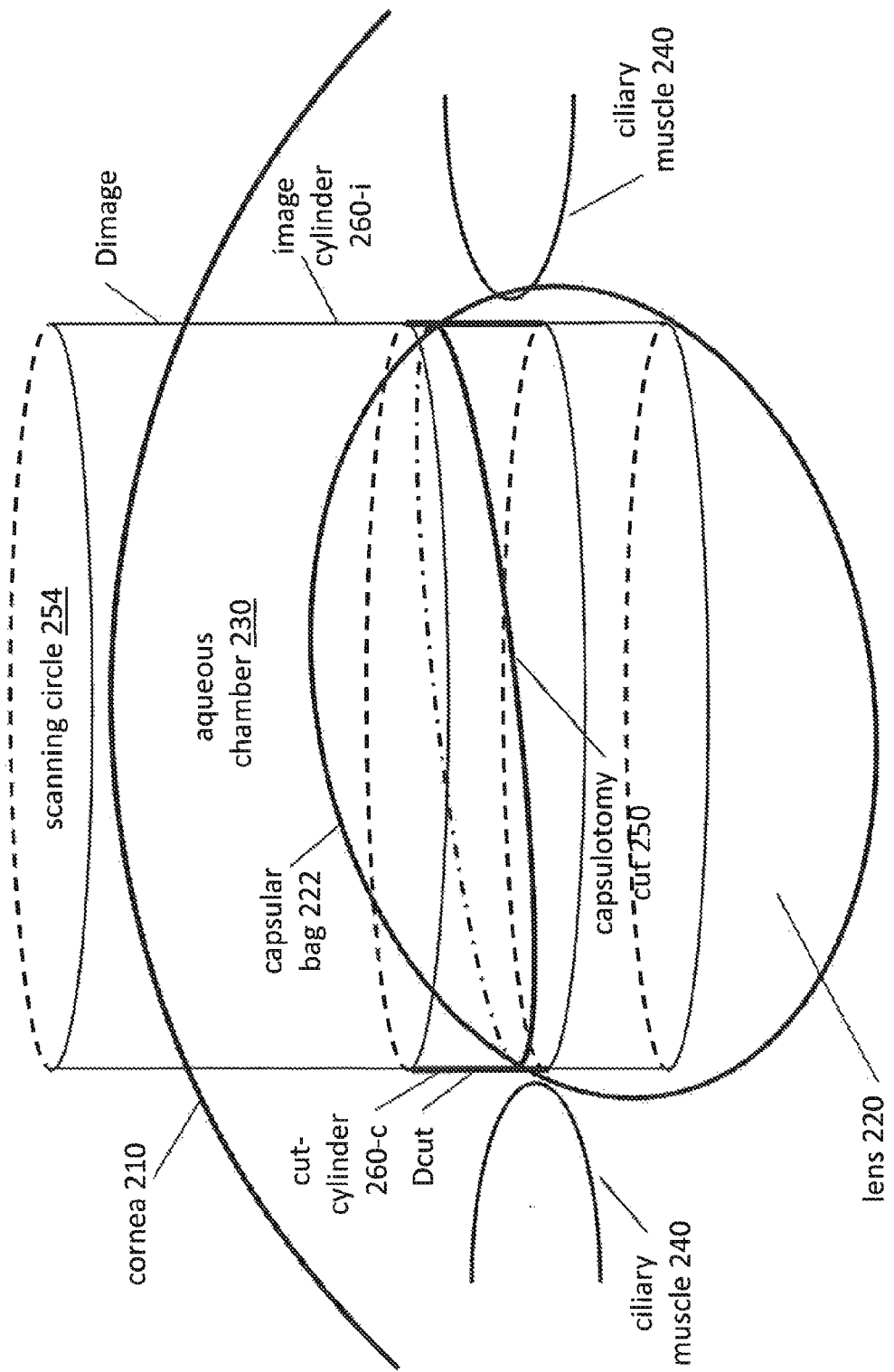

FIGS. 4A-B set the stage to illustrate the operation of the laser system 100. The imaging system 122 can image the imaged layer in an image region that can be based on a loop, an arc, a line, or a two-dimensional pattern transverse to a z-axis of the imaging system, and extends to a depth range Dimage along the z-axis of the imaging system. The imaging system 122 can support a determination of a z-depth coordinate of the imaged layer corresponding to a scanning coordinate along an image-scan.

FIG. 4A illustrates that the imaging system 122 can perform an imaging relevant for a capsulotomy step of a cataract procedure. The schematic cross section illustrates the anterior segment of the eye 1. The outermost layer is a cornea 210. A crystalline lens 220 is located behind the cornea 210, separated from it by an aqueous anterior chamber 230. The crystalline lens 220 is encapsulated in a thin capsule or capsular bag 222. The lens 220 is held in place by ciliary muscles 240. These muscles 240 also adjust the shape of the crystalline lens 220 as needed for bringing objects into focus.

As it has been described above, in order to facilitate the removal of a fragmented nucleus of the lens 220, the cataract surgery typically involves creating a circular capsulotomy cut 250 on the capsular bag 222. As a first step, the imaging system 122 can create an image 252 of the anterior segment of the eye by scanning along a scanning circle 254 and imaging the eye in a depth-range Dimage, defining an image-cylinder 260-$i$.

FIG. 5A illustrates that the image 252 typically includes an image 256 of the imaged anterior capsule layer of the lens 220 "unfolded" along a scanning variable, such as an angle along the circumference of the scanning circle 254. If a z-axis of the lens 220 is aligned with a z-axis of the laser system 100, the image 256 of the imaged layer is a flat line, indicating an essentially constant z-depth.

In other implementations, the image 252 can include the image of other ophthalmic targets, including corneal layers, portions of the sclera and even retinal layers. The zero depth level can be defined in a large number of ways, using a lens of the objective 134, a reference mirror of the imaging system 122, a level of the patient interface 136, or a level of an ophthalmic structure, such as the cornea 210.

By analyzing the image 252, a surgeon can recognize the image 256 of the imaged layer. Based on the z-depth of the imaged layer, the surgeon can decide where to direct the cutting laser beam to form the capsulotomy cut 250. The cutting laser beam is typically scanned along the same scanning circle 254 to form a cut-cylinder 260-$c$ with a depth-range Dcut, typically smaller than Dimage. This way the placement of the cut-cylinder 260-$c$ benefits maximally from the information contained in the image 252, and in particular in the image 256 of the imaged layer. The capsulotomy cut 250 is formed where the cut-cylinder 260-$c$ intersects the lens capsule 222. In practice, the cut cylinder 260-$c$ is often formed as a stack of bubble-circles, where the individual circles are created by directing the laser pulses along a circular scan-pattern at a fixed z-depth to cause photodisruption, followed by the formation of a similar circle at a slightly lesser z-depth.

In some typical cases, the image depth-range Dimage can be 5-10 millimeters, whereas the cut depth-range Dcut can be in the range of 50-200 microns, in some cases 75-150 microns, sometimes approximately 100 microns.

It is noted that the bubbles of the cut-cylinder 260-$c$ can scatter and deflect laser pulses applied in subsequent surgical steps. For example, in a cataract surgery the capsulotomy can be followed by the lens fragmentation or lysis. The bubbles of the cut-cylinder 260-$c$ can negatively impact the precision and efficiency of this subsequent lens-fragmentation by scattering the lens-fragmenting laser pulses.

Fortunately, when a z-axis of the lens 220 is parallel to a z-axis of the laser system 100, the depth range Dcut of the cut cylinder 260-$c$ can be as little as 100 microns, creating only a limited number of bubbles. Thus, in the case of a well-aligned lens 220, the bubbles of the cut-cylinder 260-$c$ introduce only a limited amount of scatter for the subsequent lens fragmentation laser pulses.

FIG. 4B illustrates, however, that in the typical surgical case the crystalline lens 220 can be tilted. This situation can occur for a variety of reasons. For example, the weight of the objective 134 can push the lens 220 sideways upon docking to the eye 1. Or, applying suction at the patient interface 136 to immobilize the eye 1 can lead to a tilting of the lens 220 as well.

FIG. 5B illustrates the image 252 of such a tilted lens 220 unfolded along the angular scanning variable of the scanning circle 254. In contrast to the non-tilted case of FIG. 5A, the image 256 of the tilted imaged layer can exhibit substantial sinusoidal oscillations. The amplitude of these oscillations can be as much as 300-500 microns. To make sure that the capsular bag 222 is cut everywhere along this sinusoid, the cut-cylinder 260-$c$ can be formed with a much enlarged depth-range Dcut, exceeding the amplitude of the sinusoid. In the above example, Dcut can be 400-600 microns to be sure that the capsular bag 222 was cut along the entire sinusoid. Clearly, this approach may create 4-6 times more photodisrupted bubbles during capsulotomy than the procedure for a non-tilted lens. Capsulotomy bubbles in such an increased number can scatter the laser pulses of the subsequent lens fragmentation to a substantial degree, threatening its precision and efficacy.

FIGS. 6A-H illustrate that some implementations of the laser system 100 can substantially reduce the number of photodisrupted bubbles by generating bubbles only in a narrow proximity of the imaged layer.

As described above, this outcome can be achieved, for example, by the imaging-based laser-controller 120 imaging the capsular bag 222, controlling the scanning of the beam of laser pulses to the points of the scan-pattern, and controlling a laser-power parameter of the laser pulses according to the distance of the points of the scan-pattern from the imaged layer.

Figure 6A:
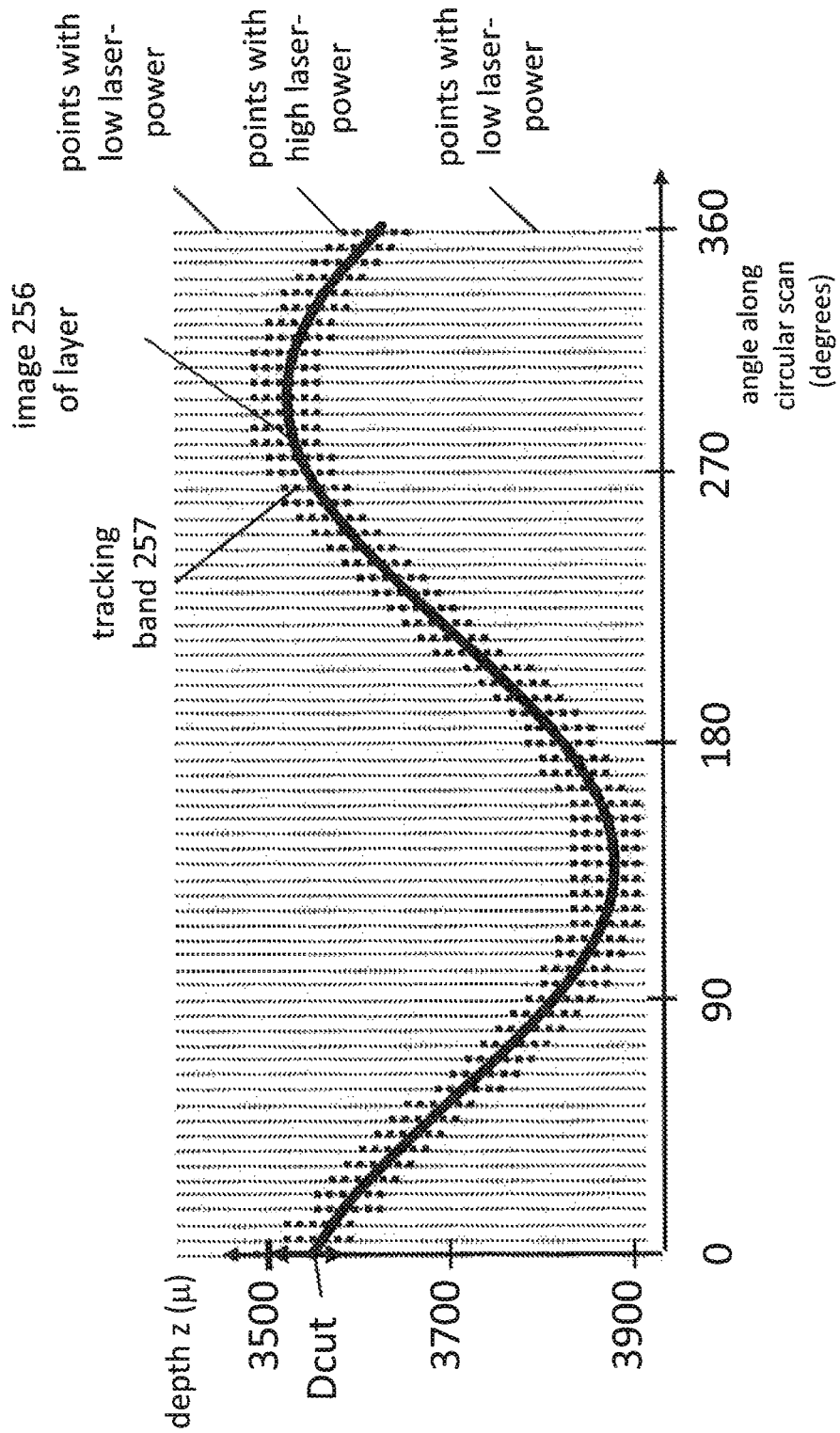
Figure 6B:
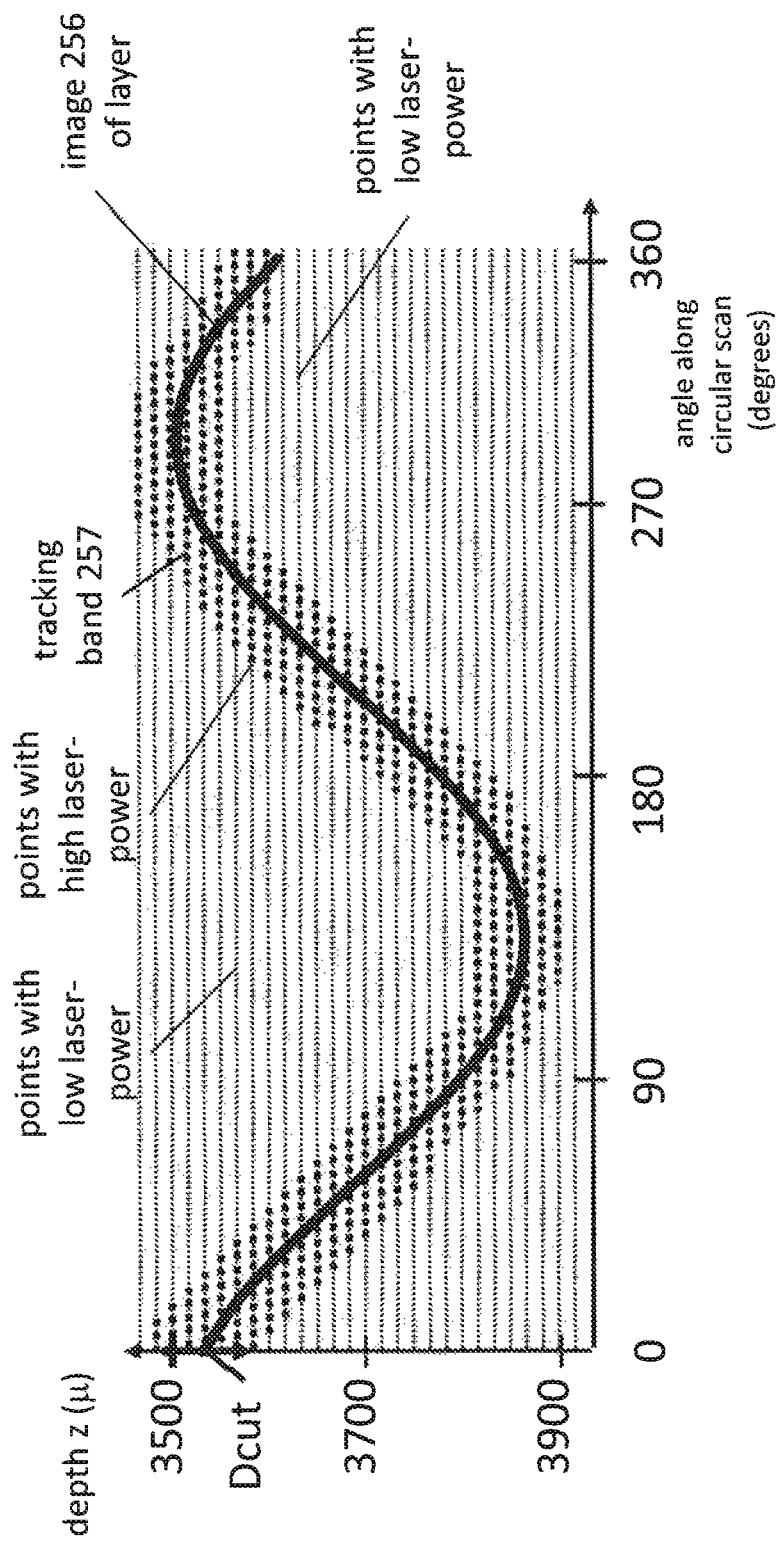

FIGS. 6A-B illustrate that as the laser pulses are directed to points of the scan-pattern, the laser controller 120 can modify or adjust a laser-power parameter of the pulses. In particular, when a laser pulse is directed to a point of the scan pattern that is within a Dcut distance from the image 256 of the imaged layer along the z axis, the laser-controller 120 can adjust its laser-power parameter to a high value, e.g. above a photodisruption threshold. Whereas, when a laser pulse is directed to a point of the scan pattern that is farther than Dcut from the image 256 of the imaged layer, the laser-controller 120 can adjust its laser-power parameter value to a low value, such as below a photodisruption threshold.

The just-described method creates bubbles only in a Dcut proximity of the imaged layer and therefore substantially reduces the number of bubbles to a value close to the number of bubbles for a well-aligned lens. For this reason, the scattering of the subsequent lens-fragmenting laser pulses by these capsulotomy bubbles is substantially reduced. Using the earlier value of Dcut being 400-600 microns for a tilted lens and 100 microns for a non-tilted lens, the present method may reduce the scattering of the lens-fragmenting bubbles by a factor of 4-6: a considerable gain in precision and control.

FIG. 6A illustrates the implementation when the scanning of the capsulotomy laser pulses of the scan-pattern is performed along the z-axis for fixed points of the circular scan. FIG. 6B illustrates the implementation when the scanning is performed along the circular scan with a fixed z-depth. This implementation can be used to create the above mentioned stacked circles. In either implementation, the points with high laser-power are placed within a tracking band 257 with a z-extent of Dcut.

FIGS. 6C-E illustrate the implementation when the laser pulses are scanned at fixed z-depths along the circular scan. A tracking band 257 can be defined as the set of points of the scan-pattern that are within the preselected distance Dcut from the image 256 of the imaged layer.

FIGS. 6D-E illustrate the laser power parameter of the pulses along the circular scan at two selected z-depths of 3600 microns and 3650 microns in an unfolded representation. The laser-controller 120 can control the laser power of the pulses that are directed to points inside the tracking band 257 to be above a photo-disruption threshold, and the laser power of the pulses that are directed to points outside the tracking band 257 to be below the photo-disruption threshold. In this embodiment, photodisrupted bubbles are only generated at points within the tracking band 257, achieving the above functionality of the laser system 100.

FIG. 6F expresses the same operation in a folded representation. Here the value of the laser power parameter is shown as a function of the angular scanning variable (typically the angle), projected on the scanning circle 254 itself. Again, for those points of the scan-pattern that lie within the tracking band 257, the laser power is high—indicated by a thick line—whereas for those points that lie outside the tracking band 257, the laser power is low.

FIGS. 6G-H illustrate a related implementation, where the laser-power controller 120 controls the laser power parameter as a function of the distance of the points from the imaged layer, wherein the laser-power is a decreasing function of the distance. FIG. 6G illustrates the implementation where this function is essentially a two-valued step-function. FIG. 6H illustrates the implementation where this function is a continuous function, its value decaying with the increasing distance from the imaged layer. In some implementations, it may be easier to control the laser power in the continuous manner of FIG. 6H.

The above-outlined implementations depend on the knowledge of the distance between the points of the scan-pattern and the imaged layer. Three stages are involved in determining this distance. First, the identity of the imaged layer is identified in the image 252 to determine the image 256 of the imaged layer. Then, the z-depth coordinate of the imaged layer is determined. Finally, the distance of the imaged layer and the points of the scan-pattern can be determined, for example, by taking the difference of the z-depth coordinates of the points of the scan-pattern and the imaged layer at the corresponding angular scanning coordinates, such as at the same angle.

Concerning the first step, the raw image 252 does not isolate or identify the imaged layer explicitly. Thus, establishing the identity of the imaged layer may necessitate an analysis of the image 252. As discussed earlier, this analysis of the image can be performed by the imaging system 122, the pattern generator 124, or the image analyzer 126, possibly assisted by an input from a system operator through the operator interface 128.

Figure 7:
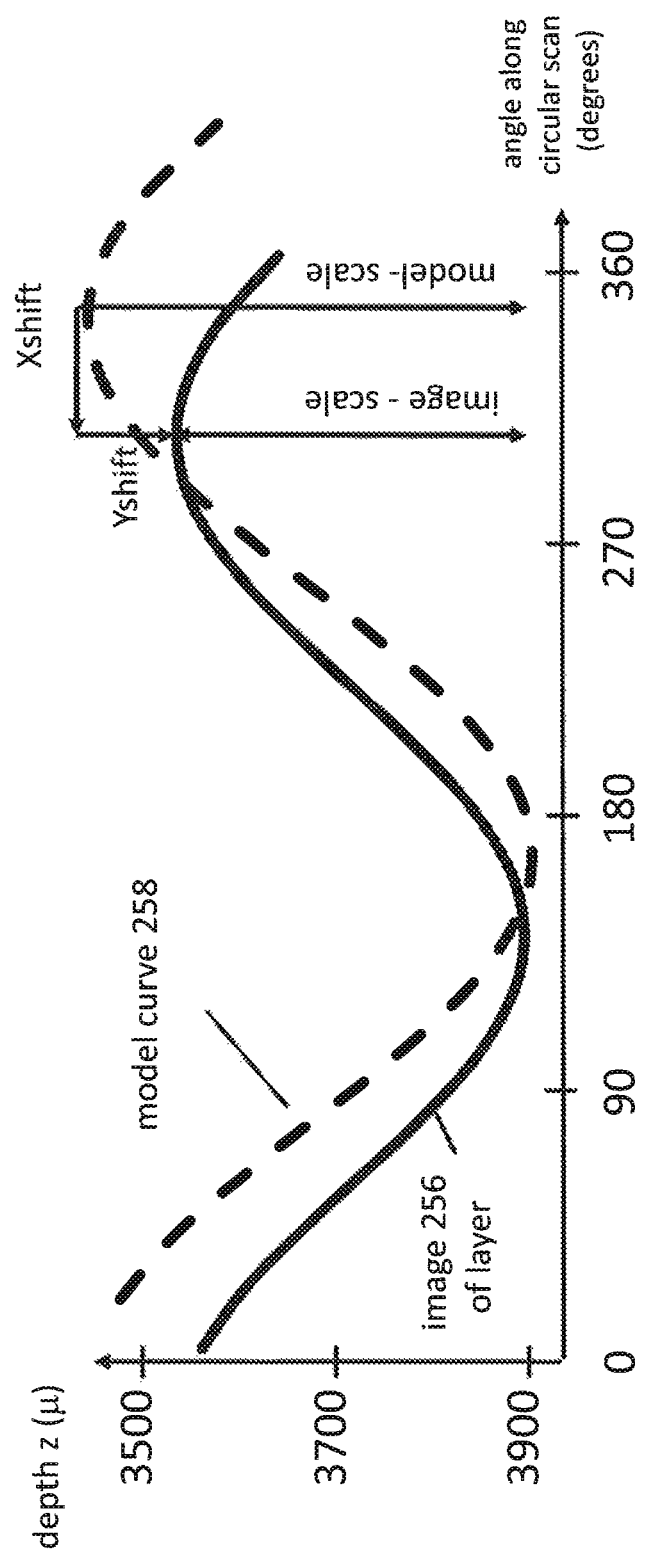
FIG. 7 illustrates a determination of the z-depth of the imaged layer by using a model curve.

FIG. 7 illustrates that the imaging system 122 can support the identification of the imaged layer and the determination of its z-depth coordinates in different ways. In some implementations the laser system 100 can include the operator interface 128 and the imaging system 122 can support the identification of the imaged layer using an input from an operator through the operator interface 128.

For example, on a graphical user interface, or GUI, the operator interface 128 can prompt the operator to fit a model curve 258 to the spots in the image 252 representing the imaged layer. Since in the case of a tilted ellipsoid-shaped lens the image 256 of the imaged layer is typically a sinusoidal curve, the operator interface 128 can display a generic sinusoidal curve 258 on the GUI and prompt the operator to fit this model curve 258 to the layer-spots in the image 252. Once the operator fitted the model curve 258 to the layer-spots in the image 252, the model curve 258 can serve as the image 256 of the imaged layer.

The operator can achieve this task through various approaches: by shifting the model curve 258 by an Xshift in the X direction (i.e. adjusting the angle along the circular scan) and by shifting the model curve 258 by a Yshift in the Y direction (i.e. adjusting the z-depth coordinate). In other implementations the operator can be prompted to adjust the scale of the model curve 258 to the scale of the sinusoidally located layer-spots in the image 252, i.e. to rescale the z-depth of the model curve 258 to fit the z-depth of the layer-spots. Many other fitting techniques can be implemented to achieve analogous functionalities.

The operator interface 128 can receive the input from the operator in many different ways, including through a keyboard, a touch-screen, a computer-communication channel, an external memory, a flash-drive, an internet connection, a speech-recognition apparatus or a wireless connection.

In other implementations, the determination of the identity and the z-depth of the imaged layer can be performed by the laser system 100 without the input of a surgeon or operator. In particular, the imaging system 122 can be configured to determine the identity and then the z-depth coordinate of the imaged layer by a processor or micro-computer performing a feature-recognition analysis of the image 252. For example, the imaging system 122 can determine the identity and coordinates of the imaged layer by locating local maxima of the gradient of the spot intensity. In other implementations, an edge-recognition algorithm can be used. In these implementations, the imaging system 122 can identify the manifold of the maximum-gradient points as the image 256 of the imaged layer without resorting to fitting a model curve 258. In some implementations, of course, the imaging system 122 can make use of a model curve 258 to identify the image 256 of the imaged layer.

In the above implementations, once the identity of the imaged layer has been determined in the image 252, the z-depth coordinates of the imaged layer can be determined in a straightforward manner, for example, by counting the pixels in the image 252, or using a reference or a look-up table.

For the image analysis, the imaging system 122 can utilize a result of a pre-surgery measurement, statistical data, video image data, ophthalmic coherence tomography image data, or a model-based computation during the determination of the z-depth.

Once the z-depth of the imaged layer has been determined, the imaging system 122 can forward the z-depth and the corresponding scanning coordinates of the imaged layer to the pattern generator 124 to carry out the last stage, the determination of the distance between the imaged layer and the points of the scan-pattern, generated by the pattern generator 124. This stage can be carried out, for example, by subtracting the z-depth coordinates of the points of the scan-pattern from the z-depth coordinates of the imaged layer that correspond to the same scanning variable, such as the same scanning angle.

Finally, having determined the distance of the points of the scan-pattern from the imaged layer, the pattern generator 124 can associate a laser-power parameter above a photodisruption threshold with those points that are closer to the imaged layer than a predetermined distance, and associate a laser-power parameter below a photodisruption threshold with those points that are farther from the imaged layer than the predetermined distance, as described in relation to FIGS. 6A-H.

In some implementations, the imaging system 122 only captures the image 252 but does not identify the imaged layer or determine its z-depth coordinates. In these embodiments, the imaging system 122 can simply forward the unprocessed image 252 to the pattern generator 124 without analyzing it. The pattern generator 124 can receive the image 252, identify the imaged layer and determine the z-depth coordinate of the imaged layer corresponding to a scanning coordinate along an image scan.

As above, in some implementations, the pattern generator 124 can determine the z-depth of the imaged layer by performing a feature-recognition analysis of the received image 252. In other implementations, the pattern generator 124 can receive an operator input through the operator interface 128 during the process of determining the z-depth of the imaged layer, as described before.

In these implementations, once the z-depth coordinates of the imaged layer have been determined, the pattern generator 124 can define a tracking band 257 as a manifold of the points of the scan-pattern that are within a predefined distance from the coordinates of the imaged layer. Then the pattern generator 124 can associate a laser-power parameter above a photodisruption threshold with points of the scan-pattern inside the tracking band 257, and a laser-power parameter below a photodisruption threshold with points of the scan-pattern outside the tracking band 257.

Yet other implementations of the laser controller 120 may include an image analyzer 126 that can determine the z-depth coordinate of the imaged layer corresponding to a scanning coordinate along an image-scan. As was illustrated in FIGS. 3B-D, the image analyzer 126 can be self-standing or at least partially integrated with the imaging system 122 or the pattern generator 124.

The image analyzer 126 can identify the imaged layer and determine the z-depth coordinate of the imaged layer by performing a feature-recognition analysis of the image 252. In other implementations, the image analyzer 126 can determine the z-depth coordinate by making use of an operator input through an operator-interface 128.

The operation of the laser system 100 can be demonstrated on the example of the capsulotomy procedure, where the imaged layer is the lens capsule 222 between the lens 220 and the aqueous anterior chamber 230. In this case, the scan-pattern corresponds to the cut-cylinder 260-c intersecting the lens capsule 222 at the capsulotomy cut 250. The pattern generator 124 can associate a photodisruptive laser-power parameter with points inside a tracking band 257 related to the intersection 250 of the cut-cylinder 260-c and the lens capsule 222, and a non-photodisruptive laser-power parameter with points outside the tracking band 257.

Figure 8:
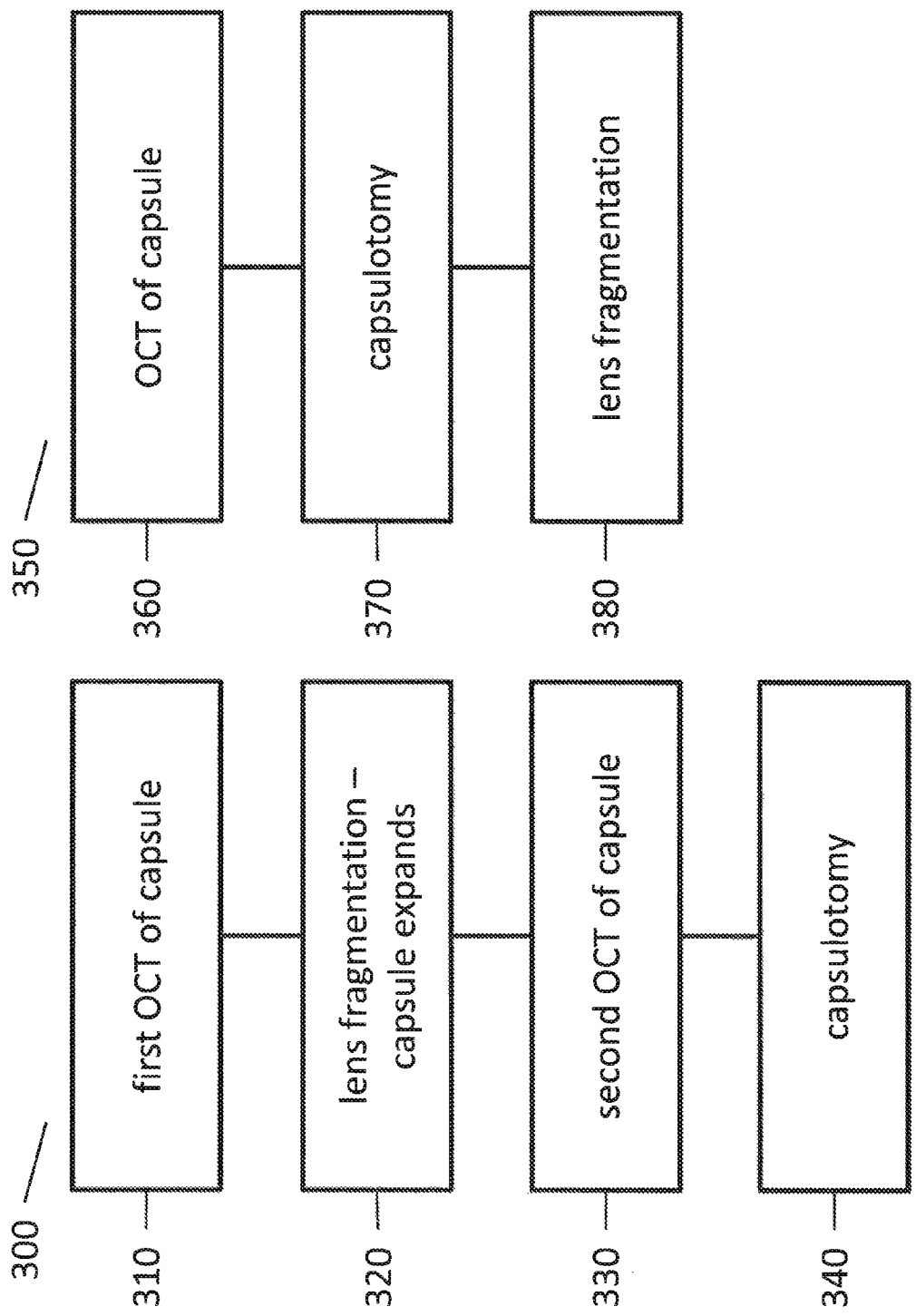
FIG. 8A-B illustrate methods of cataract surgery with the lens fragmentation and capsulotomy in different sequences.

FIG. 8A illustrates a first cataract procedure 300 performed without the benefits of the laser system 100. The cataract procedure 300 can be practiced when the capsulotomy generates an excessive number of bubbles as in FIGS. 4B-5B. To prevent excessive scattering by these capsulotomy bubbles, the lens fragmentation is performed prior to the capsulotomy. In detail, the cataract procedure 300 can include a first imaging 310 of the capsule 222, performed by an OCT procedure, followed by a lens fragmentation 320. During the lens fragmentation 320 the capsule 222 expands because of the large number of bubbles generated in the crystalline lens 220. The fragments of the lens 220 are removed through an opening, cut into the capsule 222 by a capsulotomy 340. However, since the capsule 222 has expanded during the lens fragmentation 320, the results of the first imaging 310 are not reliable anymore. Therefore, the capsulotomy 340 has to be preceded by a second imaging 330. The second imaging 330 can take up precious surgical time and increase the discomfort of the patient. Both of these factors can endanger the efficacy of the cataract procedure 300.

FIG. 8B illustrates a cataract procedure 350 with an embodiment of the laser system 100. Since the laser system 100 is capable of creating only a limited number of bubbles during the capsulotomy, the capsulotomy can be performed before the lens fragmentation. This change of sequence can reduce the surgical time to a considerable degree and thus increase the precision of the cataract procedure substantially.

In some detail, the cataract procedure 350 can include an imaging 360 of the capsule 222, e.g. by an OCT imaging system, followed by a capsulotomy 370, and completed by a lens fragmentation 380. Since the capsulotomy 370 does not deform the lens 220, there is no need for a second imaging, in contrast to the procedure 300.

Figure 9:
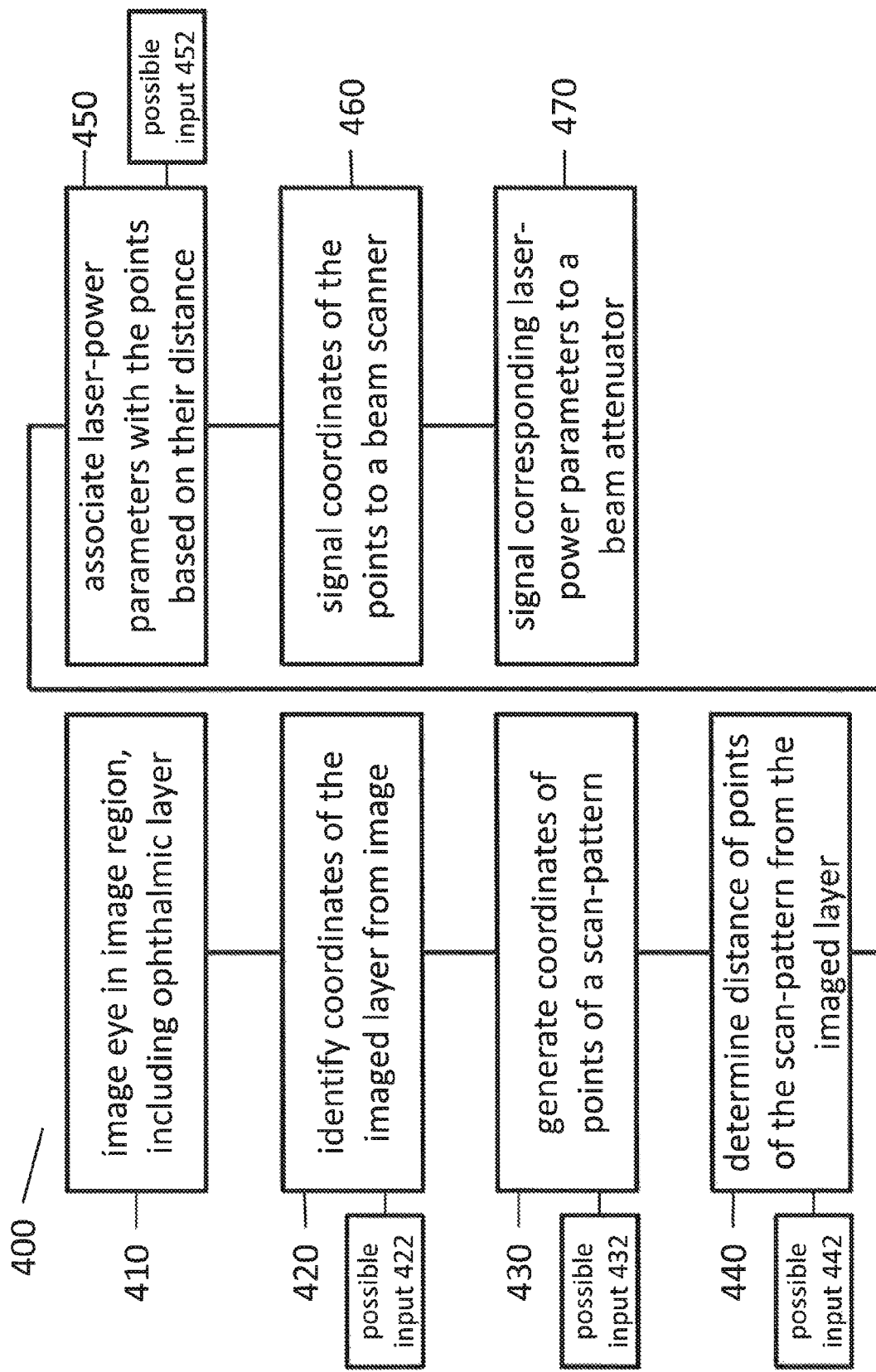
FIG. 9 illustrates a method of cataract surgery with an imaging-controlled laser system in detail.

FIG. 9 illustrates an imaging-controlled cataract method 400 in more detail. The method 400 can include an imaging 410 of an imaged ophthalmic layer in an imaged region of an eye, followed by an identifying 420 of the coordinates of the imaged layer from the image. These tasks can be performed, for example, by the imaging system 122 of the imaging-based laser-controller 120. The identifying 420 can include performing a feature-recognition analysis. In other cases, it can include receiving an operator-input through an operator interface 128. These tasks can be performed by the imaging system 122, the pattern generator 124 or the image analyzer 126.

Next, the method 400 can include a generating 430 of coordinates of points of a scan-pattern, and a determining 440 of a distance of the points of the scan-pattern from the imaged layer. These steps can be performed for example, by the pattern generator 124.

The method 400 can further include an associating 450 of laser-power parameters with the generated points based on their determined distance. The tasks 420 to 450 can include receiving possible inputs 422-452 from an operator of the laser system 100 through the operator interface 128.

The method can also include a signaling 460 of the generated coordinates of the points of the scan-pattern to the beam scanner 116 and a signaling 470 of the corresponding laser-power parameters to the beam attenuator 114.

Figure 10:
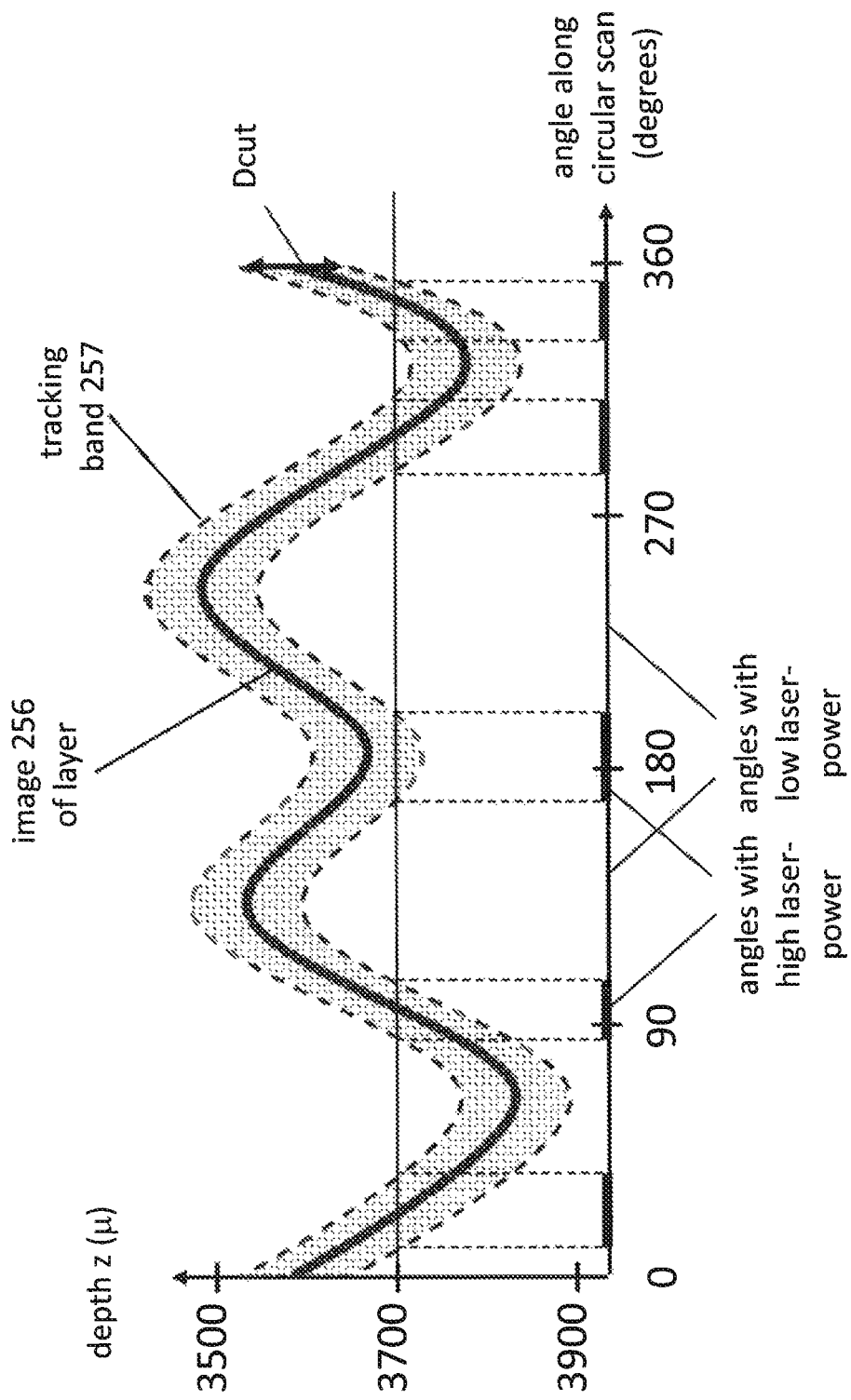
FIG. 10 illustrates a multi-extrema tracking-band laser scan-pattern after lens-fragmentation expanded the lens capsule in a non-uniform manner.

FIG. 10 illustrates the case of surgical relevance when the lens capsule 222 has an uneven shape. This situation can arise in different circumstances. For example, the docking of the patient interface 136 can cause considerable deformation of the anterior segment of the eye 1. Or an ophthalmic trauma or a prior lens fragmentation procedure can result in an uneven lens shape. In any of these circumstances, the laser system 100 can be capable of analyzing an image 256 of the imaged layer that exhibits more than two local extrema. Visibly, a simple sinusoidal model curve 258 is insufficient to identify the imaged layer and to determine its z-depth coordinate in this case. Therefore, embodiments of the imaging system 122, the pattern generator 124 or the image analyzer 126 can be capable of recognizing the imaged layer and determine its z-depth coordinate even in this more challenging case, for example, by using sophisticated feature-recognition software. Having determined and characterized the image 256 of the imaged layer can allow the pattern generator 124 to define the tracking band 257 to associate laser-power parameters with the spots of the scan-pattern accordingly.

FIGS. 11A-D illustrate that the imaging system 122 of the laser system 100 can image a region in the eye, the pattern generator 124 can generate coordinates of points of a scan-pattern for the beam scanner 116, and associate a laser-power parameter with the points of the scan-pattern depending on a distance of the points from a target-pattern.

Figures 11A, 11B:
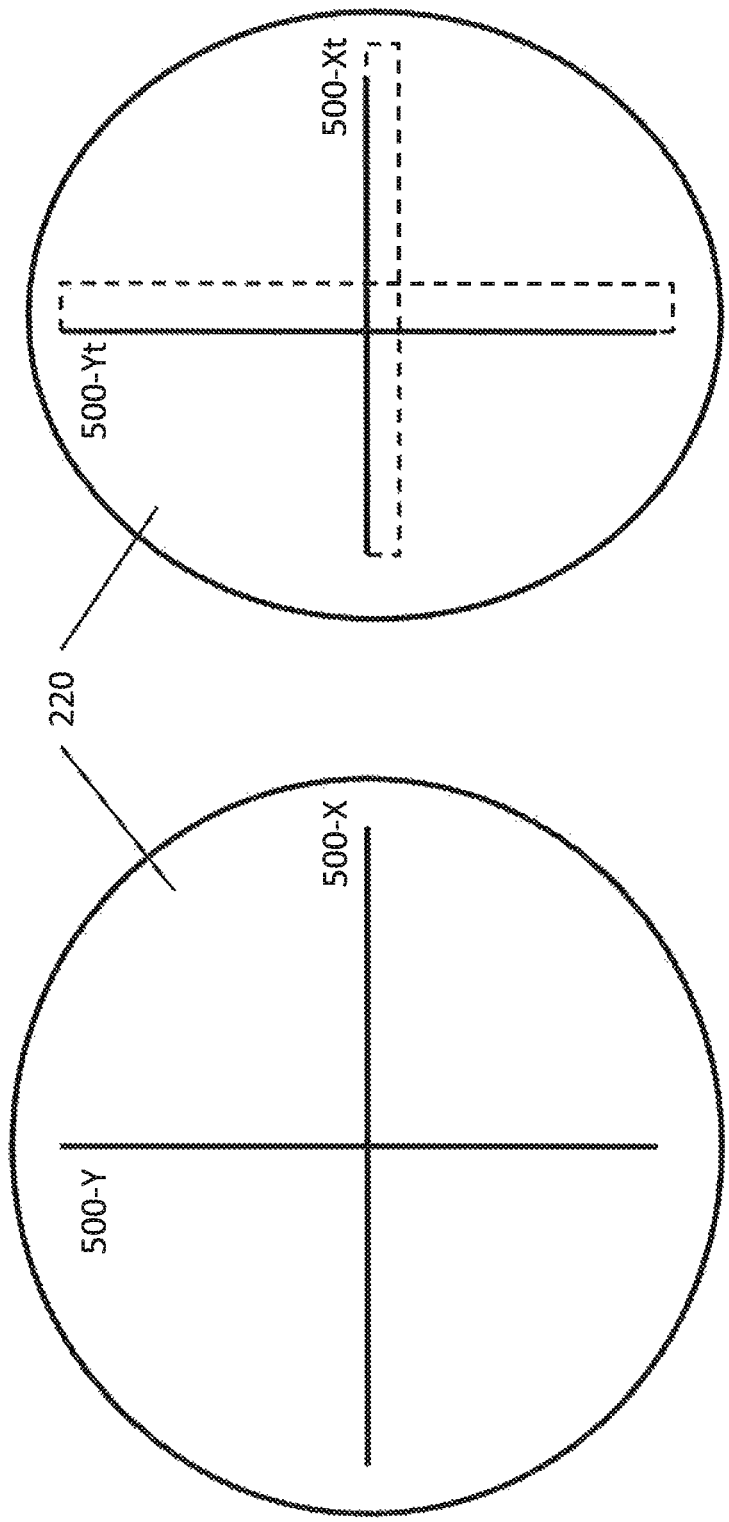
FIGS. 11A-D illustrate scan-patterns for tilted chop cuts.

An example for such a target pattern can be a chop pattern 500, including the chop-planes 500-X and 500-Y. Such chop patterns 500 can be used for lens fragmentation. FIG. 11A illustrates the case when the z-axis of the lens 220 is aligned with the z-axis of the laser system 100. In this case the chop-planes 500-X and 500-Y are also parallel to the z-axis of the laser system 100.

FIG. 11B illustrates that if the lens 220 is tilted relative to the z-axis of the laser system 100, as illustrated e.g. in FIG. 4B, then the chop planes 500-Xt and 500-Yt can be tilted as well. Since the scan-pattern often includes a first manifold of points at a first fixed z-depth, followed by a second manifold at a slightly lesser z-depth, the scan-pattern of tilted chop-planes with laser systems that cannot adjust the power of the laser pulses would create cuts into the capsular bag 222, leading to massive surgical complications.

In contrast, embodiments of the laser system 100 can associate laser-parameters depending on the distance of the points of the scan-pattern from the chop planes 500-Xt and 500-Yt.

Figure 11C:
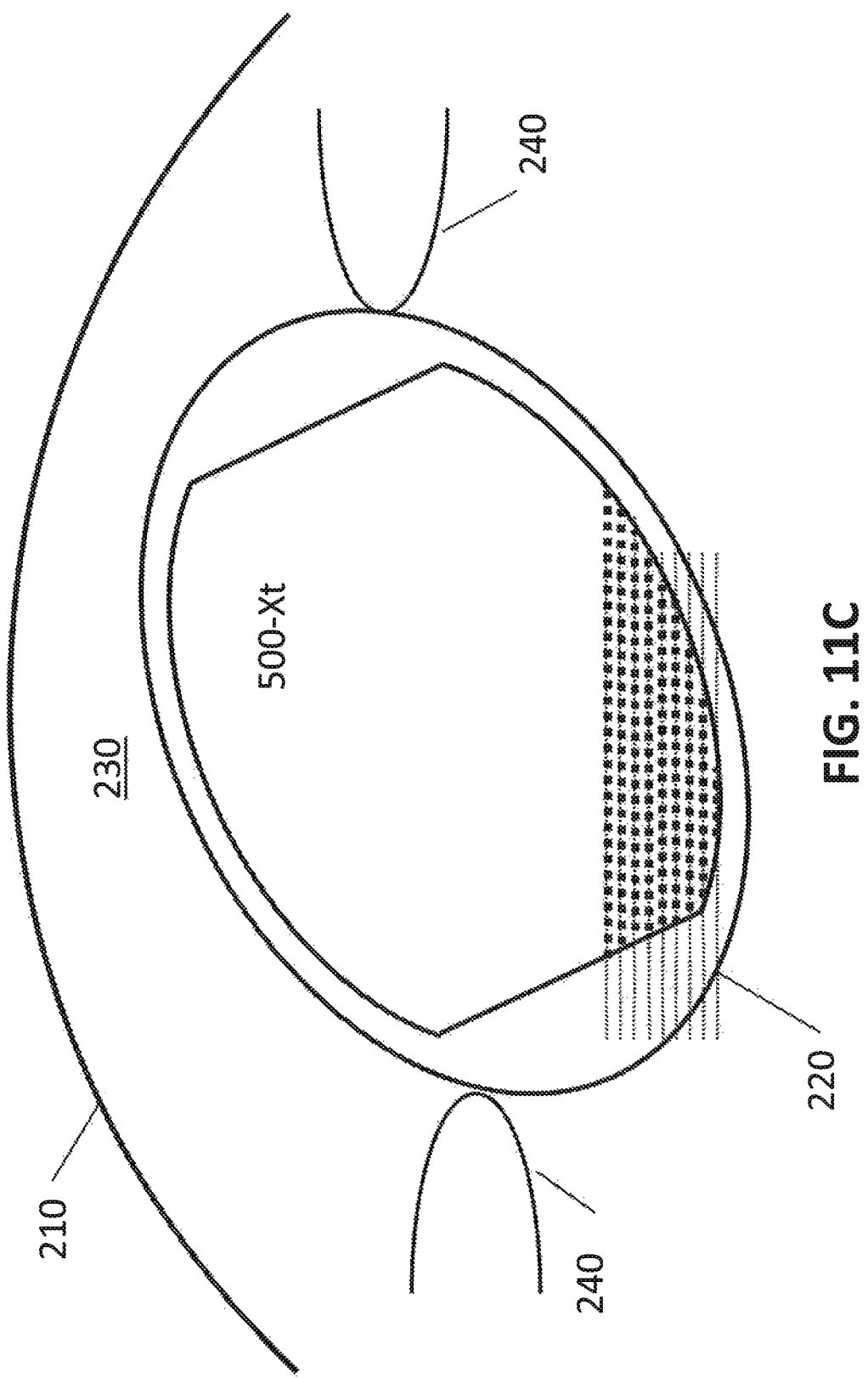
Figure 11D:
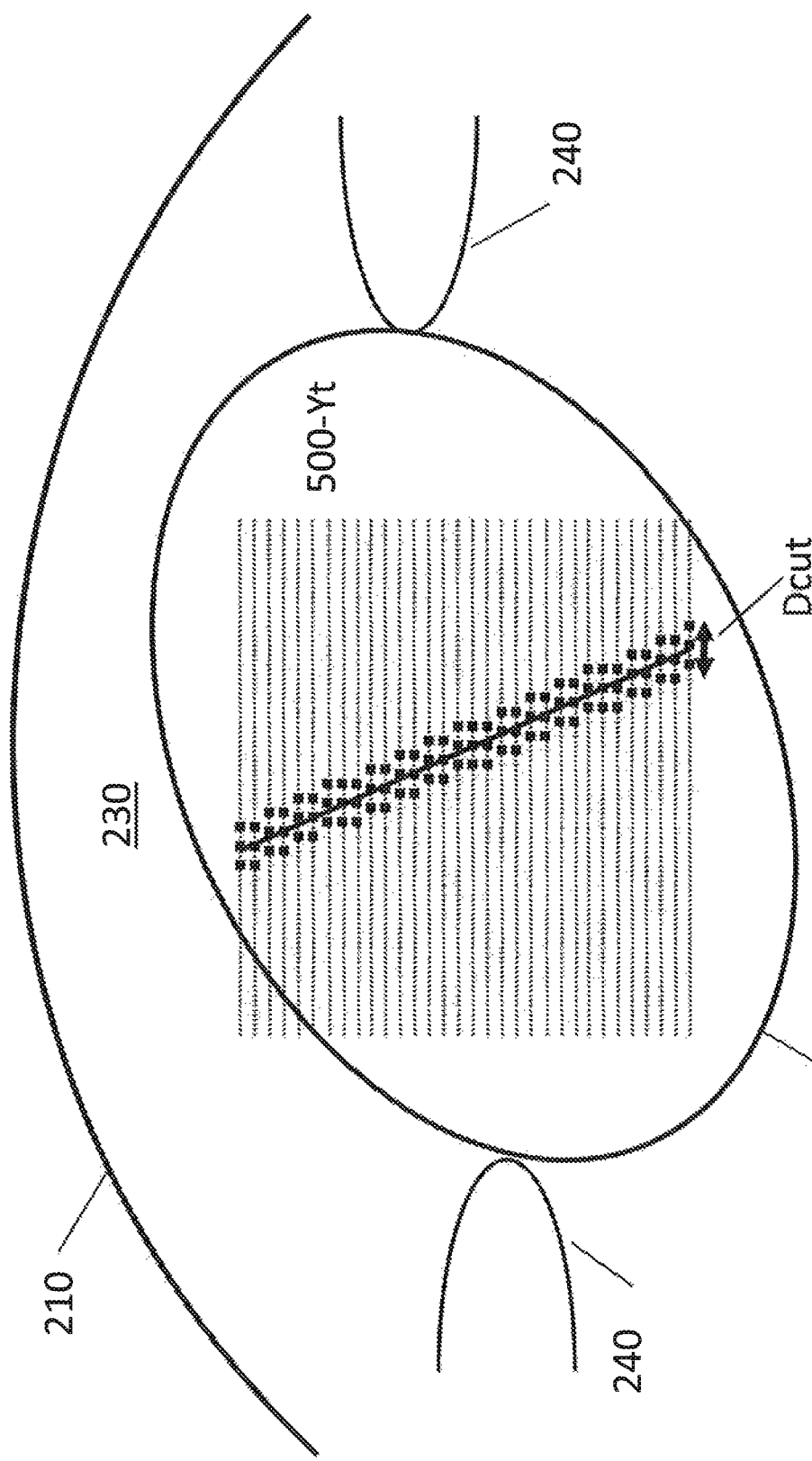

FIGS. 11C-D illustrate the points of the scan-pattern with low and high laser power, generated by the pattern generator 124 to form the tilted 500-Xt and 500-Yt chop planes. Visibly, creating cuts by adjusting the power of the laser pulses depending on their proximity to the target-pattern can avoid cutting into the capsular bag—a major surgical advantage.

FIG. 11D illustrates clearly that, as it was the case of the tracking band 257, a photodisruptive laser-power parameter can be associated with scan-points that are closer to the target-pattern 500-Xt and 500-Yt than a predetermined distance Dcut, and a non-photodisruptive laser-power parameter with the scan-points that are farther from the target-pattern than the predetermined distance Dcut.

In other implementations, the cutting surface can be a circular surface-segment, a spiral surface-segment, a corneal access cut and a limbal relaxing cut.

Figures 12A, 12B:
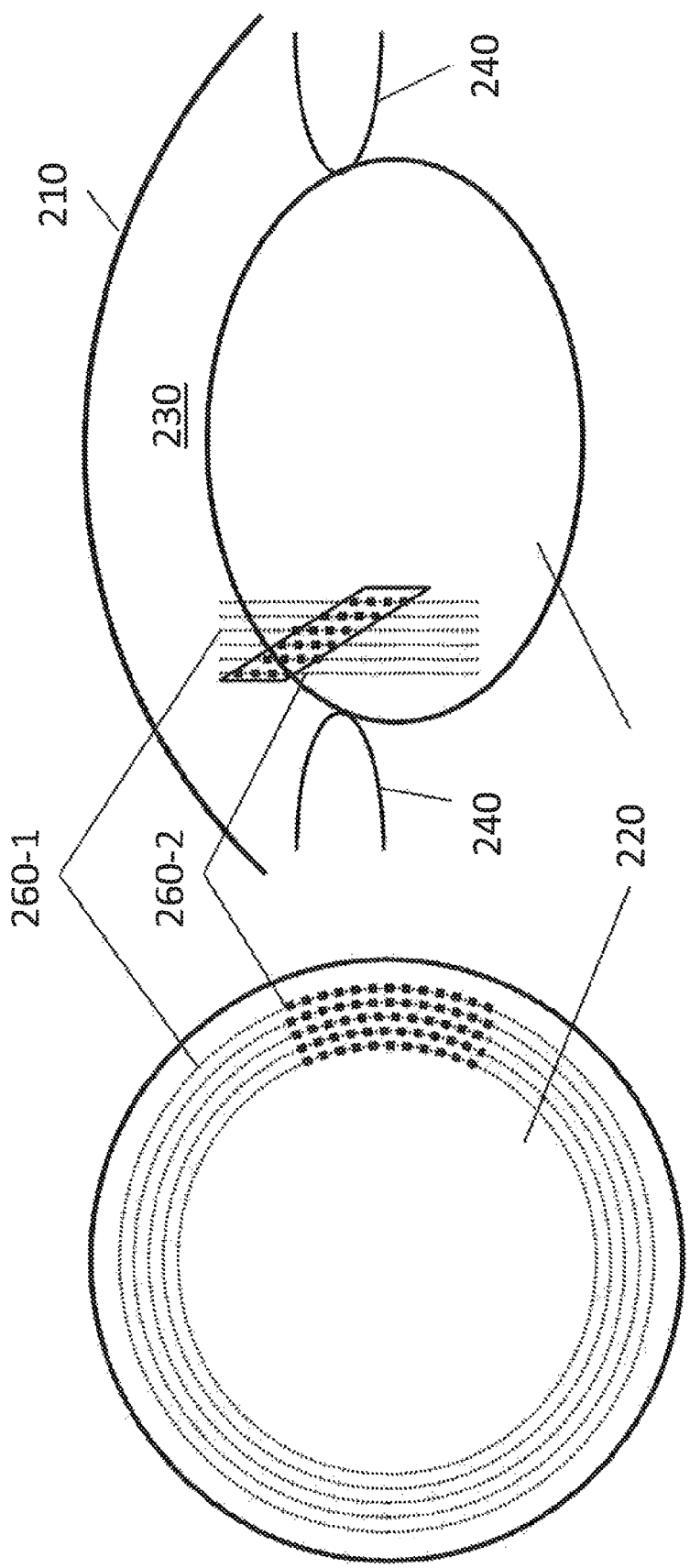
FIGS. 12A-B illustrate scan-patterns for tilted volume cuts.

FIGS. 12A-B illustrate that in some cases the target pattern 260-2 can be a target volume with an axis tilted relative to an optical axis of the laser system 100. Here, the scan pattern includes cylindrical patterns 260-1, and the laser-power parameter of the points of this scan-pattern is adjusted to form a tilted volume cut 260-2. Such a utility can be useful for correcting a refractive property of the lens 220, for example.

In some implementations, the pattern generator 124 can be configured to associate the laser-power parameters with the points of the scan-pattern depending additionally on a distance of the points from an ophthalmic layer, imaged by the imaging system 122.

While this specification contains many specifics, these should not be construed as limitations on the scope of the invention or of what can be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a subcombination or variation of a subcombination.

We claim:

1. An imaging-based laser system, comprising:
   a laser engine configured to generate a beam of laser pulses;
   an imaging-based laser-controller configured to:
   determine z-depths of a sequence of points in a scan-pattern that correspond to a layer of the eye imaged by an imaging system;
   generate a tracking band within the scan pattern defining the incision to be made in the eye, wherein a lower boundary of the tracking band has a non-uniform z-depth that varies according to the determined z-depths of the sequence of points corresponding to the imaged layer;
   cause a beam scanner to scan the beam of laser pulses to the points of the scan-pattern, and
   cause a beam attenuator to control the laser-power parameter of the laser pulses such that a laser power parameter of laser pulses in the tracking band is above a photo-disruption threshold, and a laser power parameter of laser pulses outside the tracking band is below the photo-disruption threshold.

2. The system of claim 1, wherein: the layer of the eye imaged by the imaging system is tilted relative to a z-axis of the incision to be made in the eye.

3. The system of claim 2, wherein the imaging system comprises a timedomain optical coherence tomography (OCT) system, a frequency-domain OCT system, or a spectrometer-based OCT system.

4. The system of claim 2, wherein the imaging-based laser-controller is configured to determine the z-depths of the sequence of points in the scan-pattern that correspond to the layer of the eye imaged by the imaging system by performing a feature-cognition analysis of an image of the imaged layer.

5. The system of claim 2, wherein: the imaged layer is a lens capsule between a lens of the eye and an aqueous chamber of the eye; and the tracking band corresponds to an intended capsulotomy cut intersecting the lens capsule.

6. The system of claim 1, wherein the beam attenuator comprises at least one of a Pockels cell, a polarizer-assembly, a mechanical shutter, an electro-mechanical shutter, and an energy wheel.

7. A method, comprising:
generating an image, with an imaging system, of a layer of an eye that is tilted relative to a z-axis of an incision to be made in the eye;
determining, with an imaging-based laser-controller, z-depths of a sequence of points in a scan-pattern that correspond to the image of the layer;
generating, with the imaging-based laser-controller, a tracking band within the scan pattern defining the incision to be made in the eye, wherein a lower boundary of the tracking band has a non-uniform z-depth that varies according to the determined z-depths of the sequence of points corresponding to the image of the layer;
directing, with the imaging-based laser-controller, a beam of laser pulses to the points of the scan-pattern to create the incision defined by the tracking band.

8. The method claim 7, further comprising: associating a photodisruptive laser-power parameter with points in the scan pattern that are inside the tracking band; and associating a non-photodisruptive laser-power parameter with points in the scan pattern than are outside the tracking band.

9. The method of claim 7, wherein determining z-depths of the sequence of points in the scan pattern that correspond to the imaged layer in the eye comprises performing a feature-recognition analysis to identify the imaged layer.

10. The method of claim 9, comprising: generating coordinates of the imaged layer corresponding to the scan pattern and the tracking band; signaling the coordinates to a beam scanner; and signaling laser-power parameters to a beam attenuator.

11. The method of claim 10, wherein signaling laser-power parameters to a beam attenuator comprises: signaling a photodisruptive laser-power parameter associated with points in the scan pattern that are inside the tracking band; and signaling a non-photodisruptive laser-power parameter associated with points in the scan pattern than are outside the tracking band.

12. The method of claim 7, wherein the incision defined by the tracking band results in a capsulotomy.

13. A non-transitory computer-readable medium storing instructions that, when executed, cause a processor of an imaging-based laser system to:
analyze an image of a layer of an eye that is tilted relative to a z-axis of an incision to be made in the eye;
determine z-depths of a sequence of points in a scan-pattern that correspond to the layer;
generate a tracking band within the scan pattern defining the incision to be made in the eye, wherein a lower boundary of the tracking band has a non-uniform z-depth that varies according to the determined z-depths of the sequence of points corresponding to the image of the layer;
generate signals to cause an imaging-based laser-controller system to direct a beam of laser pulses to the points of the scan-pattern to create the incision defined by the tracking band.

14. The computer-readable medium of claim 13, wherein the stored instructions, when executed, cause the processor to: associate a photodisruptive laser-power parameter with points in the scan pattern that are inside the tracking band; and associate a non-photodisruptive laser-power parameter with points in the scan pattern than are outside the tracking band.

15. The computer-readable medium of claim 13, wherein the stored instructions, when executed, cause the processor to perform a feature-recognition analysis to identify the imaged layer.

16. The computer-readable medium of claim 13, wherein the stored instructions, when executed, cause the processor to: generate coordinates of the imaged layer corresponding to the scan pattern and the tracking band; signal the coordinates to a beam scanner; and signal laser-power parameters to a beam attenuator.

17. The computer-readable medium of claim 13, wherein the stored instructions, when executed, cause the processor to signal the laser-power parameters to a beam attenuator by: signaling a photodisruptive laser-power parameter associated with points in the scan pattern that are inside the tracking band; and signaling a non-photodisruptive laser-power parameter associated with points in the scan pattern than are outside the tracking band.

* * * * *